United States Patent
Shih et al.

(10) Patent No.: US 9,353,422 B2
(45) Date of Patent: May 31, 2016

(54) USP37 INACTIVATION AS A TREATMENT FOR PLZF/RARA-ASSOCIATED ACUTE PROMYELOCYTIC LEUKEMIA

(71) Applicants: Hsiu-Ming Shih, New Taipei (TW); Wei-Chih Yang, Hualien (TW)

(72) Inventors: Hsiu-Ming Shih, New Taipei (TW); Wei-Chih Yang, Hualien (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 14/405,085

(22) PCT Filed: May 31, 2013

(86) PCT No.: PCT/US2013/043750
§ 371 (c)(1),
(2) Date: Dec. 2, 2014

(87) PCT Pub. No.: WO2013/184524
PCT Pub. Date: Dec. 12, 2013

(65) Prior Publication Data
US 2015/0148403 A1    May 28, 2015

Related U.S. Application Data

(60) Provisional application No. 61/654,948, filed on Jun. 4, 2012.

(51) Int. Cl.
C07H 21/02 (2006.01)
C07H 21/04 (2006.01)
C12Q 1/68 (2006.01)
C12N 15/113 (2010.01)
G01N 33/50 (2006.01)

(52) U.S. Cl.
CPC .......... C12Q 1/6897 (2013.01); C12N 15/1137 (2013.01); G01N 33/5008 (2013.01); C12N 2310/14 (2013.01); C12Q 2600/136 (2013.01); G01N 2333/948 (2013.01); G01N 2500/10 (2013.01)

(58) Field of Classification Search
CPC ..................................................... C12N 15/113
See application file for complete search history.

(56) References Cited

U.S. PATENT DOCUMENTS

2012/0077806 A1    3/2012 Donato et al.

OTHER PUBLICATIONS

Yen HC1, Xu Q, Chou DM, Zhao Z, Elledge SJ "Global protein stability profiling in mammalian cells" Science. Nov. 7, 2008;322(5903):918-23.

*Primary Examiner* — Amy Bowman
(74) *Attorney, Agent, or Firm* — Hsiu-Ming Saunders; Intellectual Property Connections, Inc.

(57) ABSTRACT

Method of regulating the stability and/or the level of the fusion protein PLZF/RARA are disclosed. Also disclosed are methods for identifying an agent as a regulator of the stability and/or the level of the fusion protein PLZF/RARA. Methods for identifying a therapeutic agent for treating PLZF/RARA-associated acute promyelocytic leukemia (APL) is also disclosed.

12 Claims, 7 Drawing Sheets

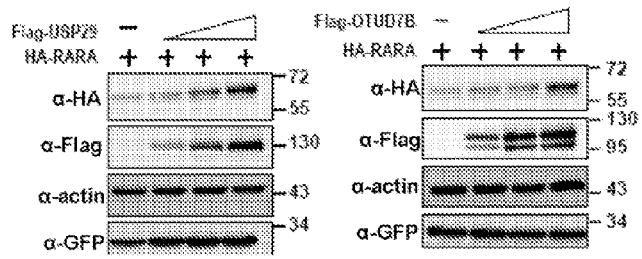
FIG. 7A
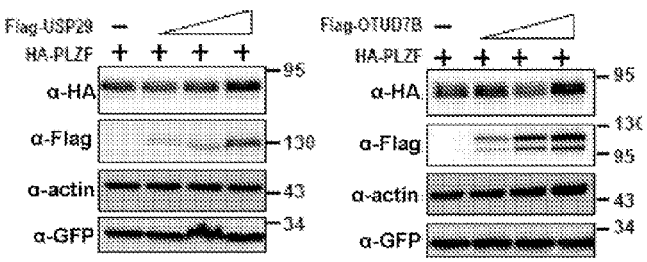
FIG. 7B
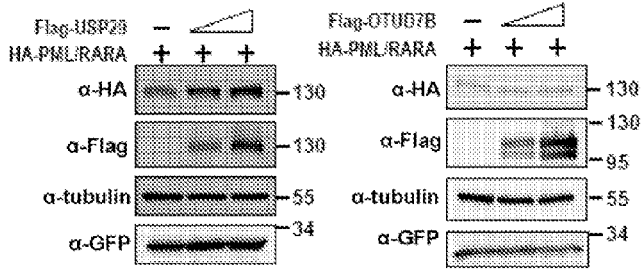
FIG. 7C
FIG. 11
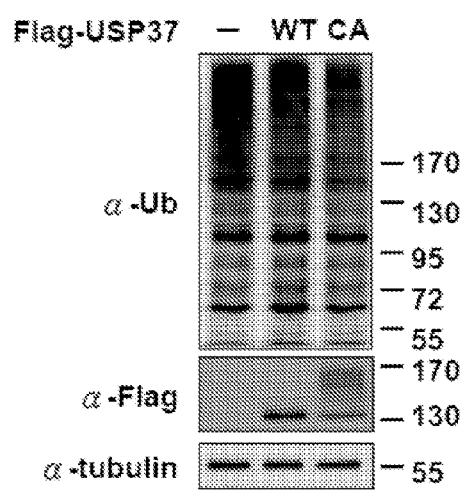
FIG. 12
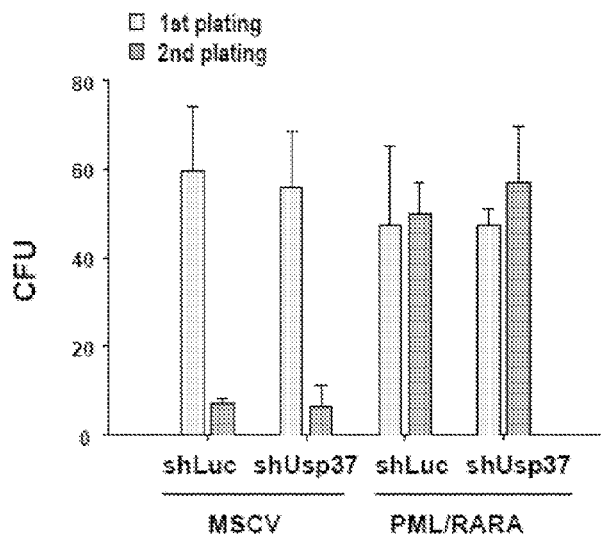

USP37 INACTIVATION AS A TREATMENT FOR PLZF/RARA-ASSOCIATED ACUTE PROMYELOCYTIC LEUKEMIA

REFERENCE TO RELATED APPLICATION

This application is a national stage application (under 35 U.S.C. 371) of PCT/US2013/043750 filed on 31 May 2013, which claims priority to U.S. provisional application 61/654, 948 filed on 4 Jun. 2012, all of which are herein incorporated by reference in their entireties.

FIELD OF THE INVENTION

The present invention relates generally to the field of regulation of the oncogenic fusion protein PLZF/RARA.

BACKGROUND OF THE INVENTION

Acute promyelocytic leukemia (APL) is a rare disease characterized by a chromosomal translocation between the retinoic acid receptor, alpha (RARA) gene and its counterpart gene (X), resulting in an aberrant fusion protein X-RARA, such as promyelocytic leukemia (PML)/RARA, promyelocytic leukemia zinc finger (PLZF)/RARA, NPM/RARA, NuMA/RARA or STAT5b/RARA. In APL patients, abnormal accumulation of undifferentiated promyelocytes is generally observed in bone marrow due to the blockage of cellular differentiation in myeloid lineage. Such differentiation arrest is in part resulted from dysregulation of key transcriptional regulators such as CEBPα involved in myeloid differentiation by those X-RARA proteins. All-trans retinoic acid (ATRA) treatment has been introduced for APL cells expressing those X-RARA fusions by promoting cellular differentiation and clinical remission of disease. Although APL cells expressing PLZF/RARA fusion are responsive to ATRA treatment for cell differentiation, PLZF/RARA-associated APL patients, distinct from other X-RARA types of APL patients, are resistant to ATRA therapy.

Ubiquitination-proteasome-dependent proteolysis is a major cellular pathway to control protein stability. Protein ubiquitination is a cascade reaction involving a group of specialized protein family called ubiquitin-activating enzyme E1, ubiquitin-conjugating enzyme E2 and ubiquitin ligase E3. Conversely, this biological process can be reversed by deubiquitinating enzymes (DUBs), which are proteases functioning by removing conjugated ubiquitin from substrates. The ubiquitination level of a substrate is regulated by its associated E3 ubiquitin ligase and/or DUB, correlating with the regulation of substrate protein stability. Thus, E3 ubiquitin ligases and DUBs are considered as potential targets for regulation of disease-associated protein stability.

DUBs have been shown to participate in several cellular functions, including DNA damage and repair, protein quality control and degradation, RNA transcription and processing, and signal transductions.

It remains unclear whether DUBs is involved in the regulation of PLZF/RARA protein stability.

SUMMARY OF THE INVENTION

The invention relates to the discovery of USP37 in regulating protein stabilization and cell transformation of PLZF/ RARA as a therapeutic target in treatment of PLZF/RARA-associated APL. A shRNA or inhibitor of USP37 or reagent(s) blocking the interaction of USP37 and PLZF/RARA may be considered as a therapeutic agent against PLZF/RARA-associated APL.

In one aspect, the invention relates to a method of assaying and/or identifying a test agent as a regulator of the stability and/or the intracellular level of the fusion protein PLZF/ RARA, comprising:

(a) providing a cell comprising: (i) a first reporter protein operably linked to a tetracycline response element and the fusion protein PLZF/RARA; and (ii) a second reporter protein operably linked to an internal ribosome entry site (IRES) and the PLZF/RARA, and treating the cell with the test agent or a vehicle control;

(b) inducing the cell to express the reporter proteins and measuring the intensity of the first reporter protein and the intensity of the second reporter protein, and calculating the ratio of the intensity of the first reporter protein versus the intensity of the second reporter protein in the presence and the absence of the test agent; and (c) identifying the test agent as a regulator of the stability and/or the intracellular level of the fusion protein PLZF/ RARA when the ratio in the presence of the test agent is less than that in the vehicle control; or (i) providing a cell constitutively expressing a transduced fusion protein PLZF/RARA and a transduced USP37, and treating the cell with the test agent or a vehicle control;

(ii) measuring the amount of the PLZF/RARA in the presence and the absence of the test agent; and (iii) identifying the test agent as a regulator of the stability and/or the intracellular level of the fusion protein PLZF/ RARA when the amount of the PLZF/RARA in the presence of the test agent is less than that in the vehicle control; or (1) providing a cell constitutively expressing a transduced fusion protein PLZF/RARA and a transduced USP37, and treating the cell with a proteasome inhibitor, which reduces the degradation of ubiquitin-conjugated proteins, and the test agent or a vehicle control;

(2) measuring the amount of ubiquitin-conjugated PLZF/ RARA within the cell in the presence and the absence of the test agent;

(3) identifying the test agent as a regulator of the stability and/or the intracellular level of the fusion protein PLZF/ RARA when the amount of the ubiquitin-conjugated PLZF/ RARA in the presence of the test agent is more than that in the vehicle control.

A constitutive promoter such as a cytomegalovirus (CMV) promoter may be used to drive a constitutive expression.

In the aforementioned step (a), the cell may be transduced with a construct comprising an insert as illustrated in FIG. 1a, where the PLZF/RARA is located between the first reporter protein and the second reporter protein, a tetracycline response element is located at the 5'-end of the whole insert, and the IRES is linked to the 5'-end of the second reporter protein.

In one embodiment of the invention, the first reporter protein is enhanced green fluorescent protein (EGFP), and the second reporter protein is red fluorescent protein (RFP).

In another embodiment of the invention, the aforementioned step (c) further comprises: (d) inhibiting the biosynthesis of the PLZF/RARA; (e) measuring the amounts of the PLZF/RARA at different time intervals to obtain the half-life of the PLZF/RARA in the presence and the absence of the test agent; and (f) validating the test agent as a regulator of the stability and/or the intracellular level of the fusion protein PLZF/RARA when the half-life of the PLZF/RARA in the presence of the test agent is shorter than that in the vehicle control.

Cycloheximide may be used to inhibit the biosynthesis of the PLZF/RARA. MG132 may be used as a proteasome inhibitor.

Further in another embodiment of the invention, the aforementioned method further comprises: a) causing a depletion of USP37 transcripts within the cell; b) assessing the impact of the depletion of the USP37 transcripts within the cell on the effect of the test agent identified; and c) validating the test agent identified as a USP37-dependent regulator of the stability and/or the intracellular level of the fusion protein PLZF/ RARA when the effect of the test agent is diminished or lost.

In another embodiment of the invention, the aforementioned step b) assesses the impact of the depletion of the USP37 transcripts on the effect of the test agent in decreasing the ratio of the intensity of the first reporter protein versus the intensity of the second reporter protein.

In another embodiment of the invention, the test agent is at least one selected from the group consisting of a small interfering RNA (siRNA) molecule, a small hairpin RNA (shRNA) molecule, an antisense molecule, and a small organic molecule.

In another embodiment of the invention, the aforementioned method further comprises:

I) contacting a human ubiquitin specific peptidase 37 (USP37) with the test agent identified; and II) measuring the human USP37 for ubiquitin hydrolase activity in the presence and the absence of the test agent to validate the test agent identified as a potential inhibitor that inhibits the activity of the USP37.

In another embodiment of the invention, the aforementioned method further evaluates the test agent identified as a potential therapeutic agent for treating PLZF/RARA-associated acute promyelocytic leukemia (APL). The evaluating step may be performed by measuring the potency of the test agent identified in inhibiting colony formation and/or proliferation of PLZF/RARA-transduced and/or PLZF/RARA-expressing hematopoietic progenitor cells.

Alternatively, the aforementioned method further comprises assessing the test agent identified for activity in inhibiting the transcript expression level of USP37.

Further in another embodiment of the invention, the cell is at least one selected from the group consisting of U937, HL60, HEK-293T cell line, a HeLa cell line, and a human primary hematopoietic cell.

In another aspect, the invention relates to a method of regulating the stability and/or the intracellular level of the fusion protein PLZF/RARA, comprising: exposing promyelocytes expressing the fusion protein PLZF/RARA to a siRNA molecule, or a shRNA molecule targeting to USP37 to decrease the stability and/or the intracellular level of the fusion protein PLZF/RARA. The shRNA may comprise a nucleotide sequence selected from the group consisting of SEQ ID NOs: 57, 56, and 54

In one embodiment of the invention, the promyelocytes are present in an acute promyelocytic leukemia patient.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 7 shows USP29 and OTUD7B regulates RARA, PLZF, and PML/RARA expression levels. Western blots of HEK-293T cells co-transfected with Flag-tagged USP29 or OTUD7B and EGFP along with HA-tagged (A) RARA, (B) PLZF, or (C) PML/RARA.

FIG. 11 shows USP37 does not significantly affect global ubiquitination. Western blot analyses of USP37 and Ub in HEK-293T cells transfected with indicated constructs. Cells were treated with 20 μM MG132 for 4 hr before harvest.

FIG. 12 shows knockdown of USP37 does not affect PML/RARA-mediated cell transformation. Bar graph represents the colony number formed from methylcellulose medium culture of mouse hematopoietic progenitor cells transduced with MSCV vector or MSCV-PML/RARA in combination with shLuc or shUsp37#2. Error bars indicate standard deviation from three independent experiments. CFU: Colony formation unit.

DETAILED DESCRIPTION OF THE INVENTION

Definitions

Figure 1:
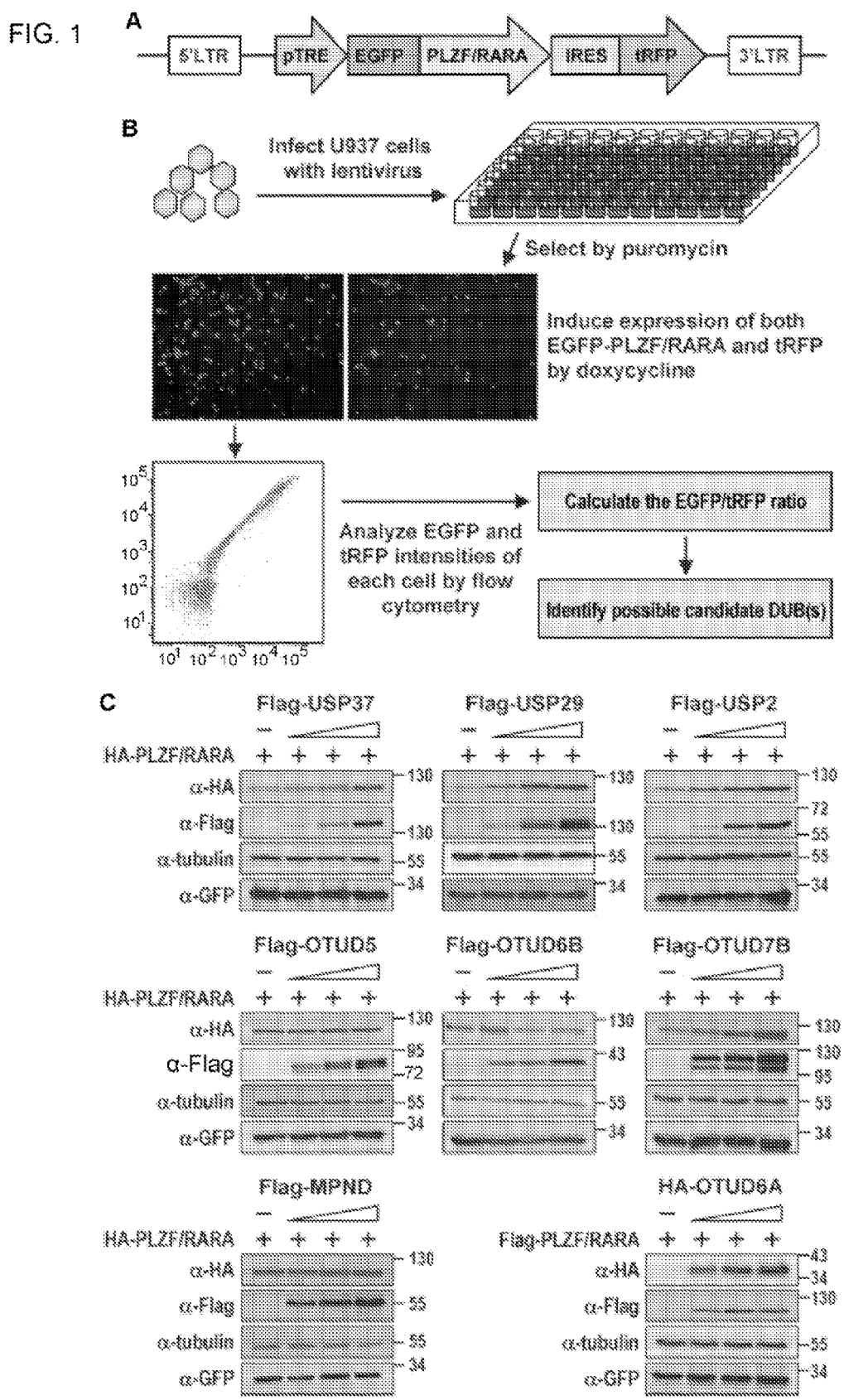
FIG. 1 shows identification of candidate DUBs in regulating PLZF/RARA protein level. (A) A schematic diagram of the cassette construct expressing EGFP-PLZF/RARA and tRFP. (B) Flowchart of functional RNAi screening for regulating PLZF/RARA level. (C) Western blots show the PLZF/ RARA levels in HEK-293T cells cotransfected with indicated DUB constructs along with CMV-EGFP. EGFP was used as cotransfection control.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term, the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

The present invention is more particularly described in the following examples that are intended as illustrative only since numerous modifications and variations therein will be apparent to those skilled in the art. Various embodiments of the invention are now described in detail. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Treating a cell with "a vehicle control" means the cell is untreated with a test agent.

Tetracycline response element is used for tetracycline-controlled transcriptional activation, which is a method of inducible gene expression where transcription is reversibly turned on or off in the presence of the antibiotic tetracycline or one of its derivatives (e.g. doxycycline).

The term "transduction". "transduced", or "transfection" shall mean the transfer of genetic material from one cell to another by means of a vector.

Cycloheximide (CHX) is an inhibitor of protein biosynthesis in eukaryotic organisms.

HL60 cell line refers to human promyelocytic leukemia cells. Human embryonic kidney 293 cells, also often referred to as HEK 293, 293 cells; U937 refers to human leukemic monocyte lymphoma cell line.

We have identified USP37 in regulating PLZF/RARA protein stability by RNAi screening. USP37 was capable of enhancing the protein level of PLZF/RARA, but not PML/RARA, through PLZF moiety. It was demonstrated that USP37 could bind and deubiquitinate PLZF/RARA directly. More importantly, USP37 knockdown attenuated PLZF/RARA-mediated target gene suppression and cell transformation. The discovery of USP37 controlling PLZF/RARA stability provide a potential therapeutic intervention for PLZF/RARA-expressing APL.

The sequences of exemplified DUBs are as follows: Human USP37 (SEQ ID NO: 17); Human USP29 (SEQ ID NO: 18); Human OTUD7B amino acid sequences (SEQ ID NO: 19). The sequence of PLZF/RARA cDNA is listed in SEQ ID NO: 59.

Examples

Without intent to limit the scope of the invention, exemplary oligos, half adaptors, instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods
Antibodies and Plasmid Constructs

The following primary antibodies were used: anti-USP37 (Bethyl Laboratories, Montgomery, Tex., USA), anti-PLZF (Merck, NJ, USA), anti-Flag (Sigma Aldrich, MO, USA), anti-HA (Covance, NJ, USA), anti-tubulin (Epitomics, CA, USA), anti-actin (Millipore, MA, USA), anti-GFP (Santa Cruz Biotechnology, CA, USA), anti-Myc (LTK BioLaboratories, Taiwan), and anti-Ub (a gift from Dr. Sheng-Chung Lee) and anti-Flag and anti-HA beads (Sigma Aldrich) for Western blotting and immunoprecipitation as where indicated. All of the shRNA constructs against DUBs and luciferase were obtained from the RNAi consortium at Academia Sinica. The pLKO-AS3-TetOn-Neo construct (the RNAi consortium, Academia Sinica) was used to generate stable TetOn-U937 cells by lentiviral infection. For the functional RNAi screening, the complementary DNA (cDNA) coding EGFP-PLZF/RARA was cloned into pLKO-AS3W-Tet-TRE-tRFP vector (the RNAi consortium, Academia Sinica) and was expressed in TetOn-U937 cells by lentiviral infection. PLZF/RARA cDNA was separately constructed into pLKO-AS4.1W-Tet-Hyg (the RNAi consortium. Academia Sinica) and pMSCVneo for lentivirus-expressing Flag-tagged PLZF/RARA in TetOn-U937 and for retrovirus expressing PLZF/RARA in mouse hematopoietic progenitor cells, respectively. The pLKO.1-shUsp37 lentivirus constructs expressing target sequences are (#1): 5'-CGCCTAAT-GTTGACTTTACAA-3'(SEQ ID NO: 1), and (#2): 5'-GCA-GAAGATGATATATTCCAGAA-3'(SEQ ID NO: 2). The cDNA constructs of USP29, OTUD5, MPND, and OTUD6A were purchased from Open Biosystems while USP37, OTUD6B, OTUD7B, and USP2 cDNAs were kindly gifted from Dr. J. Wade Harper. The cDNAs of USP2, USP29, USP37, OTUD5, OTUD6B, OTUD7B, MPND and PLZF/RARA were cloned into pCMV-3×FLAG vector for Flag-tagged protein expression. The cDNAs of OTUD6A and PLZF/RARA were inserted into pcDNA3-HA vector for HA-tagged protein expression. Ubiquitin cDNA was cloned into pCMV-3×Myc vector. USP37 and PLZF/RARA cDNAs were cloned into pMAL-c2X and pGEX-4T-2 for MBP and GST fusion protein production, respectively. The catalytically inactive USP37 (USP37 C350A) mutant was generated by site-directed mutagenesis, as described previously.31 The USP37 fragment cDNAs encoding 1-700, 301-979 and 1-300 amino-acid residues were cloned into pCMV-3×FLAG vector.

Cell Culture, Transfection, Immunoprecipitation and Western Analyses

HEK-293T and GP2-293 cells were maintained in DME with 10% FBS (Gibco, Life Technologies, NY, USA). U937, HL60 and NB4 cells were maintained in RPMI1640 with 10% FBS (Gibco). OP9 cells were maintained in alpha-MEM with 20% FBS (Hyclone, Thermo Scientific, TX, USA) and 60 μM 2-mercaptoethanol and were served as feeder layer after 4-hour treatment with 10 μg/ml mitomycin C (Sigma Aldrich). Mouse bone marrow cells were obtained from femurs of combined two male C57BL/6 mice at 8 weeks of age. Mouse hematopoietic progenitor cells were purified by negative selection with magnetic beads, according to manufacturer's instruction (R&D Systems, MN, USA) and short-term expanded by co-culture with OP9 feeder layer in IMD medium containing 10% FBS (Hyclone), 60 μM 2-mercaptoethanol, 20 ng/ml murine Scf, 20 ng/ml murine Tpo, and 20 ng/ml murine Flt-3 ligand. All cytokines were purchased from Peprotech (NJ, USA). Calcium phosphate method performed for transient transfection of HEK-293T cells. Immunoprecipitation and Western analyses were performed as described previously. In brief, transfected HEK-293T cells were harvested in NP40 lysis buffer (50 mM Trs-HCl pH 7.5, 5 mM EDTA, 1% NP40, and 150 mM NaCl) supplemented with 5 mM NEM and protease inhibitor cocktail (Sigma Aldrich). Cell lysates were immunoprecipitated with agarose beads conjugated with anti-Flag or anti-HA antibody for 2 hr at 4° C. For co-immunoprecipitation experiments of endogenous USP37 with PLZF/RARA. TetOn-U937 cells conditionally expressing Flag-tagged PLZF/RARA were harvested by NP40) lysis buffer, incubated with anti-USP37 or anti-Flag antibody for 16 hr at 4° C. and followed by adding magnetic protein G Sepharose beads (GE Healthcare, WI, USA) for additional 1 hr. Both resulting beads were washed and subjected to Western analysis with specific antibody.

GST Pull-Down and Deubiquitination Assays

GST pull-down assay was performed as described. Two μg of recombinant GST or GST-PLZF/RARA was incubated with 2 μg of MBP-USP37 and immobilized Glutathione beads (Thermo Scientific) in binding buffer (10 mM HEPES pH 7.5, 0.5 mM DTT, 0.5 mM EDTA, 0.1% NP-40, and 50 mM NaCl) for 4 hr at 4° C. After washing three times, the samples were then subjected to Western analysis. For in vitro deubiquitination assay, poly-ubiquitinated PLZF/RARA proteins immunoprecipitated from HEK-293T cells expressing Flag-tagged PLZF/RARA and Myc-tagged Ub were incubated with recombinant USP37 protein in 100 μl of deubiquitination buffer (50 mM Tri-HCl pH 8.0, 5 mM $MgCl_2$, and 1 mM DTT) for 2 hr at 37° C. The deubiquitination reaction was stopped by adding SDS sample buffer and bound proteins were extracted from beads for Western analysis.

Viral Infection and Replating Assay

Lentiviral supernatants were prepared as described previously. In brief, 12 μg lentiviral DNA construct, 3 μg pMD2.G (Addgene, MA, USA), and 9 μg psPAX2 (addgene) were co-transfected in HEK-293T cells with 60% confluency in 10-cm dish. Likewise, retroviral supernatants were prepared from 60% confluent HEK-293 cells in 10-cm dish co-transfected with 9 µg pVSV-G, and 12 µg retroviral DNA constructs. Both lentivirus and retrovirus were concentrated by ultra-centrifugation with 20,000 rpm for 2 hr at 4° C. Mouse hematopoietic progenitor cells co-cultured with OP9 feeder were infected by retrovirus carrying PLZF/RARA construct with addition of 0.8 µg/ml polybrene (Sigma Aldrich). After 16 hr infection, culture medium was replaced by fresh differentiation culture medium, which is IMDM supplemented with 10% FBS, 20 ng/ml SCF, 10 ng/ml of each IL3, IL6 and GM-CSF. For serial infection, the resulting cells were further infected with lentivirus expressing indicated shRNA for additional 16 hrs and replaced with fresh differentiation culture medium. After selection by G418 (500 mg/ml) and puromycin (1 mg/ml), cells were subjected for quantitative real time PCR analyses. For replating assay, transduced mouse hematopoietic progenitor cells (10,000 cells/ml) were then plated to MethoCult (Stem Cell Technology) medium supplemented with 20 ng/ml SCF, 10 ng/ml of each IL3, IL6, and GM-SCF, and 1 mg/ml G418 and 2 µg/ml puromycin for selection. After 7 days, cells were replated for additional 7 days and the expression level of cell surface marker were analyzed by FACS with fluorochrome-conjugated antibodies (c-kit/CD117, clone 2B8; Mac-1/CD11b, clone M1/70; Gr-1/Ly-6G, clone RB6-8C5; all purchased from BioLegend).

Quantification of PLZF/RARA-Regulated Gene Expression

Total cellular RNAs were extracted by TRIzol reagent (Invitrogen) and RNA of each sample was subsequently reverse transcribed using THERMOSCRIPT™ reverse transcription-PCR system (Invitrogen), according to manufacturer's instruction. Reverse transcription PCR product was used for quantitative real-time PCR analyses (Applied Biosystems 7500 Life Technologies) with specific primers, as following: Cebpa forward 5'-AGGAACTTGAAGCACAAT-3' (SEQ ID NO: 3) and reverse 5'-ACACAGAGACCAGATACA-3' (SEQ ID NO: 4); Cebpb forward 5'-CGGGGTTGTTGATGTTTT-3' (SEQ ID NO: 5) and reverse 5'-CATACGCCTCTTTTCT-CATAG-3' (SEQ ID NO: 6); Cebpe forward 5'-CAAGAAG-GCAGTGAACAA-3' (SEQ ID NO: 7) and reverse 5'-GCTGAGTCTCCATAATGC-3' (SEQ ID NO: 8); Usp37 forward 5'-CTCATCAGTGTTGTCAGT-3' (SEQ ID NO: 9) and reverse 5'-TCCAGGTCATTGTAAGTG-3' (SEQ ID NO: 10); Hprt forward 5'-GATTAGCGATGATGAACCAGGTT-3' (SEQ ID NO: 1) and reverse 5'-CCTCCCATCTCCTTCAT-GACA-3' (SEQ ID NO: 12). Hprt gene expression was used as an internal control for normalization. The RT-PCR product was used for semiquantitative PCR analyses with specific primers as following: PLZF/RARA forward 5'-TGAA-GACGTACGGGTGCGAG-3' (SEQ ID NO: 13) and reverse 5'-TGTAGATGCGGGGTAGAGGG-3' (SEQ ID NO: 14); actin forward 5'-CCTAGAAGCATTTGCGGTGG-3' (SEQ ID NO: 15) and reverse 5'-GAGCTACGAGCTGCCT-GACG-3' (SEQ ID NO: 16). The PCR products were then resolved by 1.5% agarose gel containing ethidium bromide.

Statistical Analysis

Statistical analyses were carried out by using SAS® 9.1.2 (SAS institute Inc) with two-tailed student t test. Two-tailed student t test was used here to calculate the EGFP/tRFP intensity ratio between experimental and control groups. To eliminate a false positive rate occurred from multiple testing, we introduced Bonferroni's adjustment to correct p-values obtained from t test, therefore, data with p-value <0.0001 was considered as statistical significant.

Results

RNAi Screening Identifies DUBs Modulating PLZF/RARA Protein Level

To monitor PLZF/RARA protein level in cells, we have generated U937 myeloid leukemia cell line carrying a cassette in which both EGFP-PLZF/RARA and tRFP driven by an internal ribosome entry site were induced to express by addition of doxycycline (FIG. 1A). This cell line was infected individually with ~400 distinct lentiviruses expressing specific shRNA clones targeting to 83 human DUBs in 96-well plates. Following the puromycin selection for shRNA-expressing cells and doxycycline (Dox) induction for both EGFP-PLZF/RARA and tRFP expressions, the cells in each well were subjected to 96-well flow cytometry analysis for measuring the relative expression levels of both EGFP-PLZF/RARA and tRFP proteins (FIG. 1B). In this screening, EGFP intensity was used to measure PLZF/RARA protein level while tRFP expression level was served as an internal control to normalize EGFP intensity. To reduce the off-target effects from shRNA clones, DUB targeted by at least three shRNA clones showing significant effect (by p-values) on reducing EGFP/tRFP ratio was chosen as a candidate for further study. Eight candidate DUBs, including MPND, OTUD5, OTUD6A, OTUD6B, OTUD7B, USP2, USP29, and USP37 were initially identified (Table 1). To further validate whether these candidate DUBs regulate PLZF/RARA protein expression, each candidate DUB was ectopically expressed with PLZF/RARA in HEK-293T cells. OTUD6A, OTUD7B, USP2, USP29, and USP37 could enhance PLZF/RARA protein expression in a dosage dependent manner while MPND, OTUD5, and OTUD6B failed to do so (FIG. 1C), suggesting that OTUD6A, OTUD7B, USP2, USP29, and USP37 are potential DUBs to regulate PLZF/RARA protein level.

USP37 Modulates PLZF/RARA Protein Level Through PLZF Moiety

Figure 6A:
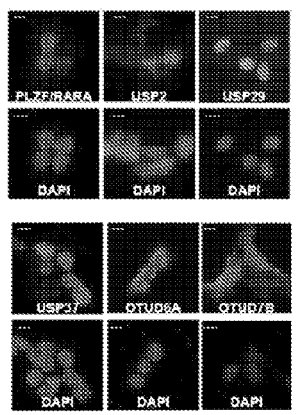
FIG. 6 shows sub-cellular localizations of DUBs and PLZF/RARA. (A) Representative images of HEK-293T cells transfected with HA-PLZF/RARA, Flag-USP2, Flag-USP29, Flag-USP37, Flag-OTUD7B or HA-OTUD6A. Images were acquired by a Nikon TE2000-U fluorescent microscope (Nikon, NY, USA) and Image-Pro Plus software (Media Cybernetics. Inc. MD, USA). Bar, 10 μm. (B) Western blots show individual endogenous DUBs in subcellular fraction of HEK-293T cells. Antibodies for USP29. OTUD6A, and OTUD7B were purchased from ABGENT (CA, USA). Antibody for cMyc was purchased from Sigma-Aldrich (MO, USA)
Figure 6B:
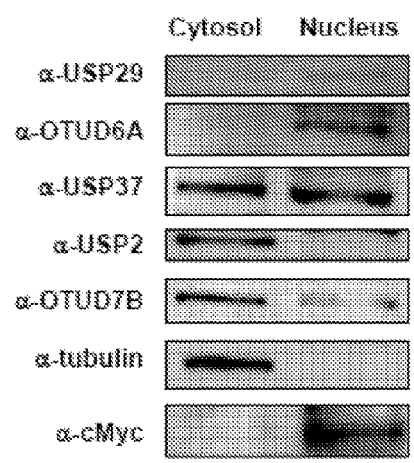

Because PLZF/RARA proteins are mainly localized in the nuclear compartment, we next examined the subcellular localization of these five candidate DUBs for possible direct interaction and regulation of PLZF/RARA. The results of immunofluorescence and western analyses demonstrated that those candidate DUBs, including USP29, USP37. OTUD6A and OTUD7B, were present in the nuclear compartment (FIGS. 6A-B). OTUD6A was distributed in the peri-nuclear region (FIG. 6A). These results implicated possible involvement of USP29, USP37 and OTUD7B in PLZF/RARA regulation via a direct association.

Figure 2:
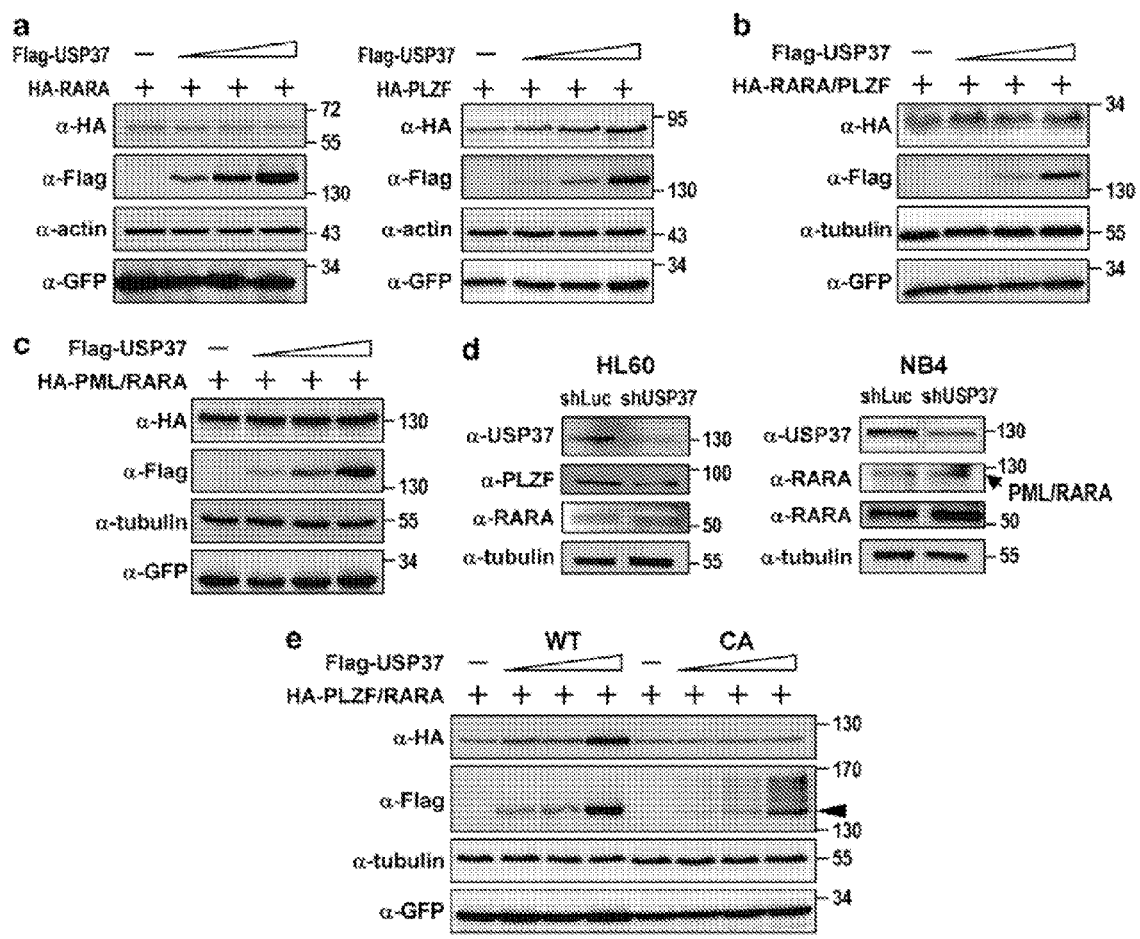
FIG. 2 shows that USP37 regulates PLZF/RARA expression level. (a-c) Western blots of HEK-293T cells transfected with Flag-tagged USP37 and EGFP along with HA-tagged PLZF or RARA (a), or HA-tagged RARA/PLZF (b) or HA-tagged PML/RARA (c). (d) Immunoblotting shows endogenous level of USP37, PLZF, RARA and PML/RARA in indicated cells with shUSP37 or shLuc. Arrow indicates PML/RARA. (e) Immunoblots show PLZF/RARA levels in HEK-293T cells cotransfected with USP37 WT or catalytic mutant C350A (CA). Arrowhead indicates non-modified band of USP37 CA mutant.

Because PLZF/RARA is a fusion protein resulted from reciprocal chromosomal translocations between PLZF and RARA genes, it is possible that USP29, USP37 or OTUD7B could modulate PLZF/RARA protein level through the moiety of PLZF or RARA, or both portions. To test these possibilities, HA-tagged PLZF or RARA was transiently co-expressed with Flag-tagged USP29, USP37 or OTUD7B in HEK-293T cells. PLZF protein but not RARA protein was elevated by USP37 in a dose-dependent manner (FIG. 2a), while expression of USP29 or OTUD7B enhanced RARA protein but not PLZF protein (FIGS. 7A-7B). Furthermore, increasing USP37 expression was unable to alter the protein level of the reciprocal chromosomal translocation product, RARA/PLZF (FIG. 2b), nor affected the protein level of another abnormal fusion protein PML/RARA (FIG. 2c). In contrast, expression of USP29 but not OTUD7B could increase PML/RARA protein level (FIG. 7C). These data suggest that USP37 may stabilize PLZF/RARA through the PLZF moiety, whereas USP29 may exert similar function via the RARA moiety in cells. We further substantiated the specificity of USP37 targeting to the PLZF moiety by USP37 knockdown experiments. USP37 depletion reduced endogenous PLZF level but not RARA level in HL60 cells (FIG. 2d, left panel). In contrast, USP37 knockdown failed to significantly alter the protein level of endogenous PML/RARA and RARA in NB4 cells (right panel), a cell line derived from long-term cultures of human APL. The findings that USP37 conferred the specific regulation on PLZF/RARA, but not on PML/RARA level, led us to focus on the study of USP37 in regulating PLZF/RARA.

Figure 8:
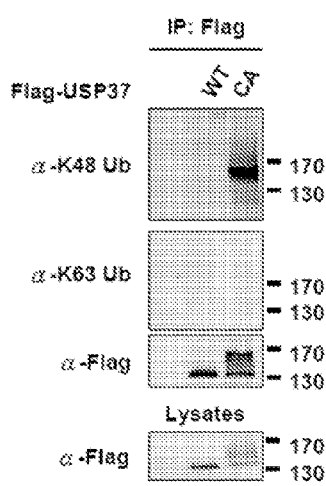
FIG. 8 shows USP37 CA mutant is modified by K48-linkage polyubiquitination. Western blots show PLZF/RARA ubiquitination in HEK-293T cells transfected with indicated constructs.
Figure 9:
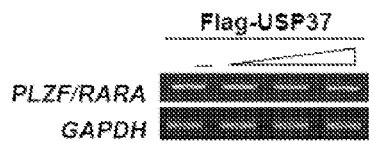
FIG. 9 shows USP37 does not affect PLZF/RARA mRNA level. RT-PCR analysis of HEK-293T transfected with PLZF/RARA along with increasing levels of Flag-USP37 construct. GAPDH was used as a loading control.

We next examined whether USP37-regulated PLZF/RARA protein level is relevant to its protease catalytic activity. USP37 catalytically inactive mutant, converting Cys350 to Ala (CA), was generated to examine for PLZF/RARA regulation. The USP37 CA mutant was impaired to enhance PLZF/RARA protein level as compared with WT (FIG. 2e), indicating the importance of USP37 catalytic activity for PLZF/RARA regulation. Overexpression of USP37 CA mutant rendered USP37 multiple-band shifts. These slowly migrating bands were K48-linkage ubiquitinated USP37 proteins, as evidenced by western blot analysis with antibodies against specific ubiquitin linkage (FIG. 8). In addition, PLZF/RARA mRNA level was not altered by USP37 overexpression (FIG. 9), suggesting that the regulation of PLZF/RARA by USP37 was not at the mRNA level.

USP37 Regulates PLZF/RARA Protein Level Via a Direct Protein Interaction

Figure 3:
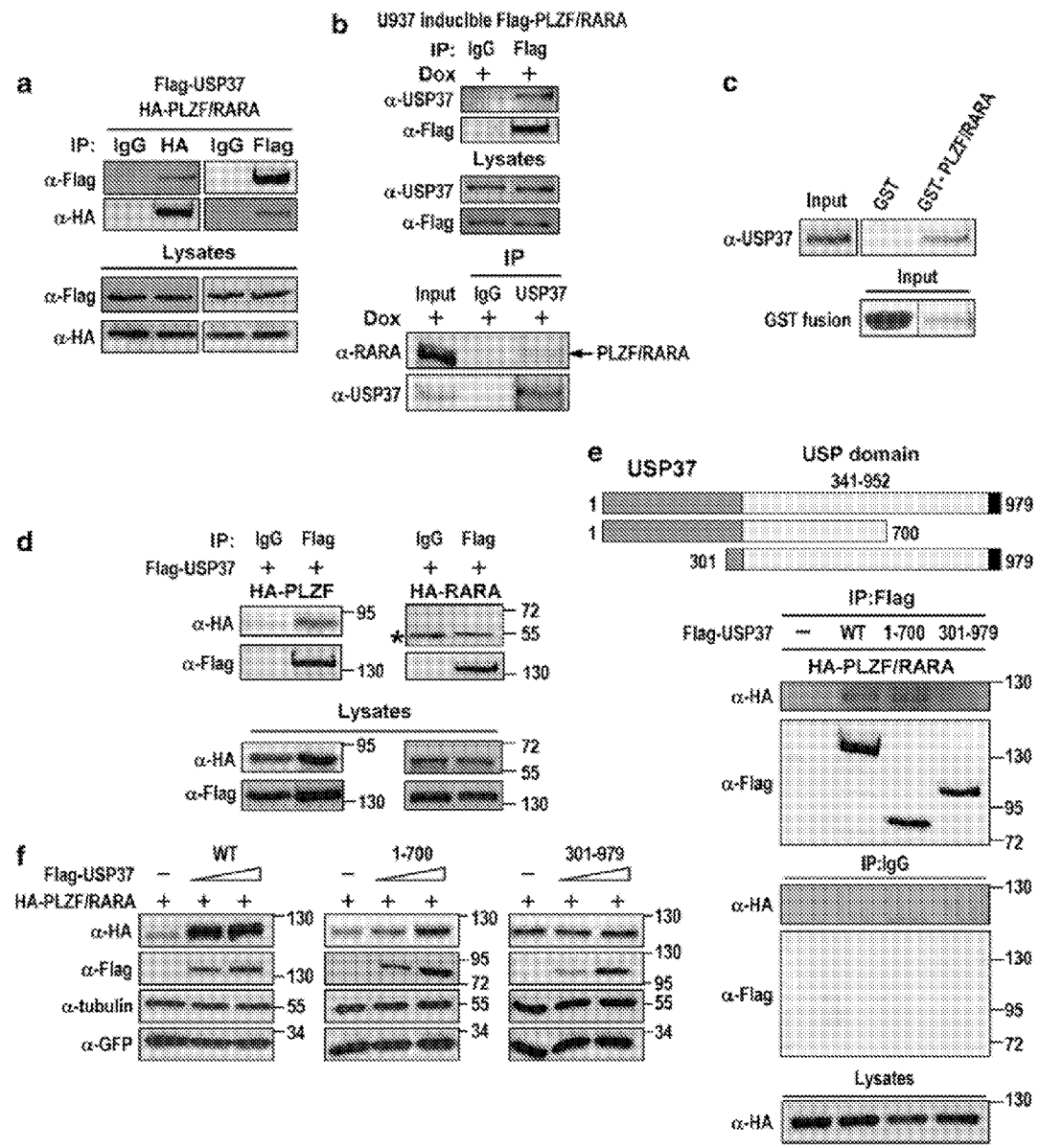
FIG. 3 shows that USP37 interacts with PLZF/RARA. (a) Western blots show the complex formation of Flag-tagged USP37 and HA-tagged PLZF/RARA in HEK-293T cells transfected with indicated constructs. (b) Western blots show the interaction of endogenous USP37 and flag-tagged PLZF/ RARA in TetOn-U937 cells with or without 0.5 mg/ml doxycycline induction for 16 h and precipitated by anti-USP37 or anti-Flag antibody. (c) Immunoblotting shows USP37 pulled down by GST-PLZF/RARA. Input represents the 10% amount of recombinant USP37 protein subjected to binding assays. Coomassie blue staining shows GST fusion proteins used for each binding reaction. (d) Western blots show the complex formation of USP37 with PLZF but not with RARA in HEK-293T cells transfected with indicated constructs. Asterisk indicates IgG heavy chain from immunoprecipitation. (e) Diagram view of wild-type and deleted mutants of USP37. The USP domain is indicated. Western blotting analysis of immunoprecipitated complex from HEK-293T cells transfected with indicated constructs. (f) Western blots show the PLZF/RARA levels in HEK-293T cells cotransfected with USP37 WT or deletion mutants.

Given that USP37 regulates PLZF/RARA protein steady-state level, we further assessed whether USP37-regulated PLZF/RARA protein level is through a protein interaction between USP37 and PLZF/RARA. We first demonstrated that USP37 and PLZF/RARA can form complexes in cells. The results of co-immunoprecipitation experiments revealed that overexpressed Flag-tagged USP37 could be detected in the immunocomplex of HA-PLZF/RARA (FIG. 3a), and the interaction of USP37 and PLZF/RARA was further confirmed by reciprocal immunoprecipitation experiments (FIG. 3a). We further substantiated the complex formation of PLZF/RARA with endogenous USP37, using U937 cells conditionally expressing Flag-tagged PLZF/RARA by adding doxycycline. Endogenous USP37 could form complexes with PLZF/RARA in cells by immunoprecipitation with either anti-USP37 or anti-Flag antibody (FIG. 3b). To test whether USP37 binding to PLZF/RARA is through a direct interaction, in vitro GST pull-down assay was performed using GST-fused PLZF/RARA and MBP-fused USP37 recombinant proteins. MBP-USP37 could be pulled down by GST-PLZF/RARA but not by GST (FIG. 3c), suggesting that USP37 can directly interact with PLZF/RARA.

To demonstrate the importance of USP37-PLZF/RARA interaction for PLZF/RARA protein regulation, we performed the domain mapping study. In line with the result that USP37 enhanced PLZF but not RARA protein steady-state level (FIG. 2a). Flag-tagged USP37 could precipitate HA-tagged PLZF but not HA-tagged RARA (FIG. 3d). On the front of USP37, we generated and tested N and C-terminal deletion mutants of USP37 for PLZF/RARA interaction (FIG. 3e). The results of co-immunoprecipitation experiments showed that N-terminal deletion mutant (301-979), although it contains the entire USP domain, significantly reduced the PLZF/RARA interaction (FIG. 3e, lane 4), while USP37 C-terminal deletion mutant (1-700) bound to PLZF/RARA with the extent slightly lesser to WT (lanes 2 and 3). The protein steady-state level of USP37 (301-979) fragment was not significantly affected by USP37, compared with (1-700) fragment or WT (FIG. 3f). These results provide a nice correlation between the binding and regulation of PLZF/RARA protein by USP37.

USP37 Regulates the Protein Stability and Ubiquitination of PLZF/RARA

Figure 10:
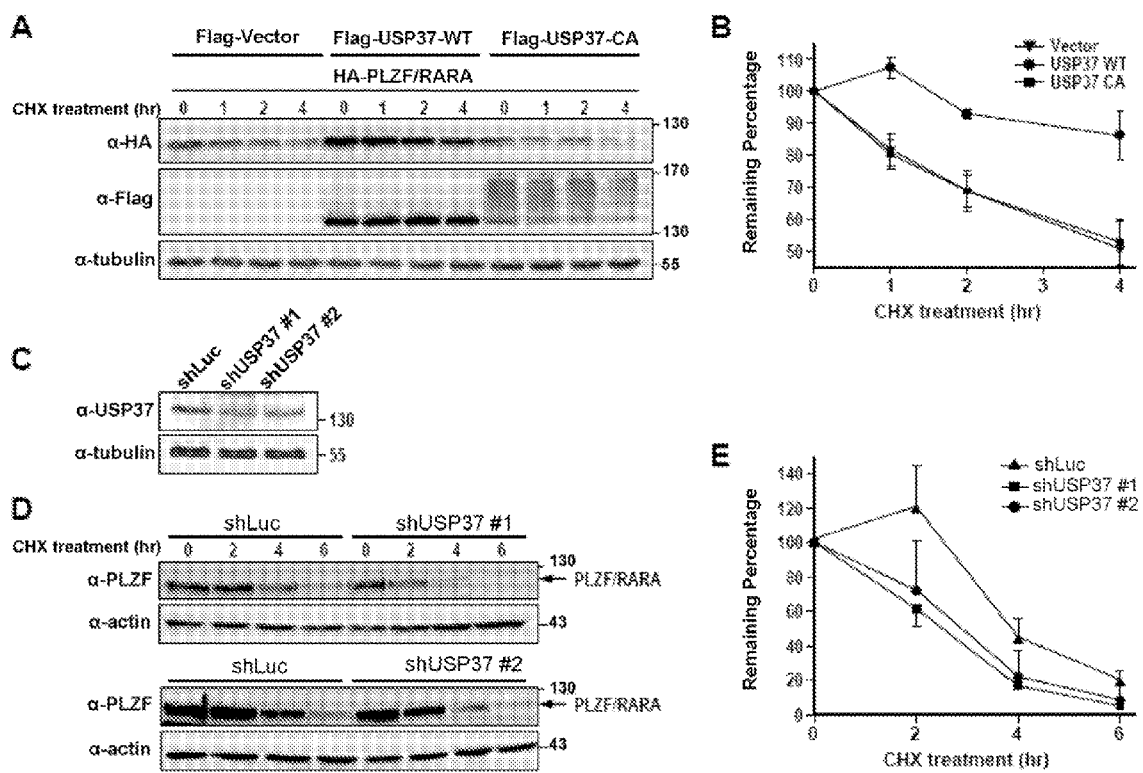
FIG. 10 shows USP37 regulates PLZF/RARA protein stability. (A) Western blotting represents HAPLZF-RARA expressions in HEK-293T cells cotransfected with indicated constructs and treated with 50 mM CHX for the indicated periods of time. (B) The plot shows quantification of the PLZF/RARA protein amount relative to levels in untreated cells in (A). (C) Western blotting analyses of endogenous USP37 in Flag-PLZF/RARA-inducible TetOn-U937 cells infected with lentivirus expressing shLuc, shUSP37 #1, or shUSP37 #2. (D and E) Western blots show Flag-PLZF/RARA level in TetOn-U937 cells with USP37 knockdown. The expression of PLZF/RARA was induced by Dox for 16 hr in TetOn-U937 cells expressing indicated shRNAs and further treated with 25 mM CHX for the indicated periods of time (D). The plot shows quantification of the PLZF/RARA amount relative to levels in CHX untreated cells.

We next examined the effect of USP37 on PLZF/RARA protein half-life, cycloheximide (CHX)-chase experiments showed that USP37 WT, but not CA mutant, prolonged PLZF/RARA protein half-life in HEK-293T cells (FIG. 10A-10B). Knockdown of USP37 by shRNA clones identified from initial RNAi screening (FIG. 10C and Table 1) showed a reduction of PLZF/RARA protein half-life in U937 cells (FIG. 10D-10E). These results clearly demonstrate that USP37 enhances PLZF/RARA protein stability. Table 1 shows candidate DUBs identified by RNAi screening with significant hits.

TABLE 1

| Gene | shRNA clone | p-value | Targeted sequence | SEQ ID NO: |
|---|---|---|---|---|
| MPND | 1 | $1.15 \times 10^{-25}$ | CTTTGCAGCCATCAACAAGTT | 20 |
| | 2 | $1.18 \times 10^{-11}$ | CTGGTGGAAGTAACATCCTTT | 21 |
| | 3 | 0.0152 | GCCAGAAACTGGACAAGTACA | 22 |
| | 4 | $4.45 \times 10^{-5}$ | CTCTGTCAAGTACAAAGGCCA | 23 |
| | 5 | 0.0175 | CGTTCAACGTGGCTGTTTCTA | 24 |
| OTUD5 | 1 | 0.0554 | CCATCATTCAAACCAGGGTTT | 25 |
| | 2 | $2.53 \times 10^{-5}$ | CTGACCTTGCTGCATTCCTTT | 26 |
| | 3 | $7.06 \times 10^{-10}$ | GCATGCTGAATTGGGCATGAA | 27 |
| | 4 | 0.0896 | CAACAGGAATACCTAGACAGT | 28 |
| | 5 | $1.09 \times 10^{-11}$ | CACTAGCTTCTTTGGAATCTT | 29 |
| OTUD6A | 1 | 0.3307 | GAAACGAAATTCGAGGGAAAT | 30 |
| | 2 | $1.74 \times 10^{-21}$ | CATGATCTACTGCGACAACAT | 31 |
| | 3 | $1 \times 10^{-12}$ | CGACAGTAGCATTGAATCTGT | 32 |
| | 4 | $9.01 \times 10^{-10}$ | CACCAACTAAGATTTGGTCAT | 33 |
| OTUD6B | 1 | $5.8 \times 10^{-8}$ | CGAGAAGAACGGATAGCTGAA | 34 |
| | 2 | $1.12 \times 10^{-6}$ | CGATGAGACTAATGCAGTGAA | 35 |
| | 3 | $2.69 \times 10^{-13}$ | GCAAAGCTACTAACAGGTGTT | 36 |
| | 4 | $3.05 \times 10^{-10}$ | GCTGACTACTAAGGAGAATAA | 37 |
| | 5 | $2.65 \times 10^{-5}$ | CAGGGCATGAAGAATGCTGTT | 38 |
| OTUD7B | 1 | $1.86 \times 10^{-5}$ | CGGGACTTGATGCTGCGGAAA | 39 |
| | 2 | $3.02 \times 10^{-5}$ | CGGTCCCATGTCTCCTCCAAT | 40 |
| | 3 | $5.27 \times 10^{-21}$ | CCCAACTCAGACCAAATGCAA | 41 |
| | 4 | 0.0035 | GCAAGGAGGCTAAACAAAGTT | 42 |
| | 5 | 0.0705 | CCTGTATATGAGAGCCTTGAA | 43 |
| USP2 | 1 | $1.26 \times 10^{-7}$ | CCGCGCTTTGTTGGCTATAAT | 44 |
| | 2 | $1.4 \times 10^{-7}$ | GCTCACAACATTTGTGAACTT | 45 |
| | 3 | $1.17 \times 10^{-5}$ | CCCATTGCTAAGCGAGGTTAT | 46 |
| | 4 | $5.31 \times 10^{-13}$ | CCATGCTGTTTACAACCTGTA | 47 |
| | 5 | 0.112 | CCTCGGCGTTTGCATTTGTAA | 48 |
| USP29 | 1 | $5.04 \times 10^{-5}$ | CTGGTGAAGAATAACGAGCAA | 49 |
| | 2 | 0.0004 | CCCTCAATCAGTCTACAGAAT | 50 |
| | 3 | $3.14 \times 10^{-5}$ | TGTGTGGAGTATCTTGGTGTA | 51 |
| | 4 | 0.0061 | GCAGTGTATTGAGGAGAGCAT | 52 |
| | 5 | $1.69 \times 10^{-5}$ | CCACTTTAGAGATAGGGCAAT | 53 |
| USP37 | 4 | $2.02 \times 10^{-5}$ | GCTACCGAGTTAAGTCTTCAA | 54 |
| | 3 | 0.2158 | CCCTAACTTCTCTGGCCTATT | 55 |
| | 2 | $2.04 \times 10^{-6}$ | GAGAATAAAGTCAGCCTAGTA | 56 |
| | 1 | $3.33 \times 10^{-8}$ | CCGGATTTGCAGAAGATGATA | 57 |
| | 5 | 0.218 | CGGAGTGGCTACATCTTCTTT | 58 |

Figure 4A:
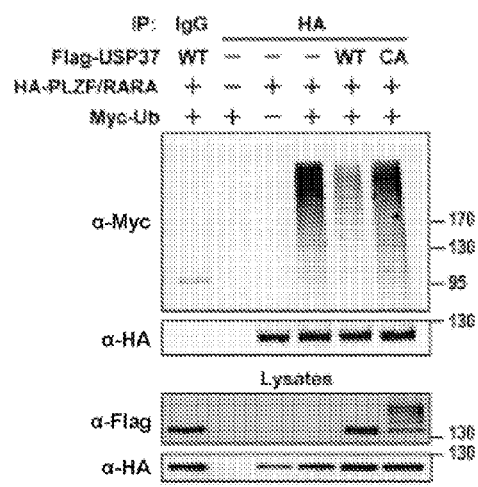
FIG. 4 shows that USP37 deubiquitinates PLZF/RARA. (A) Western blots show PLZF/RARA deubiquitinated by USP37 in HEK-293T cells transfected with indicated constructs and treated with 20 mM MG132 for 4 h before harvest. (B) Immunoblotting shows PLZF/RARA ubiquitination in TetOn-U937 cells with USP37 knockdown. TetOn-U937 cells expressing FLAG-PLZF/RARA were infected with lentivirus carrying shLuc or shUSP37#1 construct and treated with 10 mM MG132 for 4 h before harvest. (C) Immunoblotting shows in vitro deubiquitination of poly-ubiquitinaled PLZF/RARA immunoprecipitated from HEK-293T cell lysates incubated with purified USP37 WT or CA mutant protein for 2 h. Input represents the 10% amount of immunoprecipitated proteins subjected to deubiquitination assays. Coomassie blue staining shows USP37 proteins used for each deubiquitinating reaction.

The findings that USP37 catalytic activity is required for increasing PLZF/RARA protein stability led us to test whether USP37 modulates PLZF/RARA protein ubiquitination level. Overexpression of USP37 WT, but not CA mutant, significantly decreased the ubiquitination of PLZF/RARA in HEK-293T cells (FIG. 4A). The effects of USP37 on PLZF/

Figure 4B:
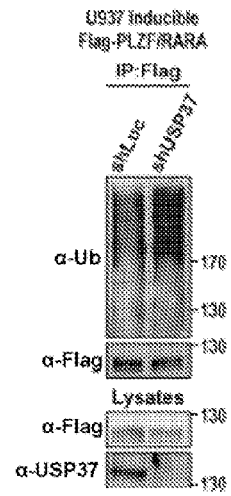
Figure 4C:
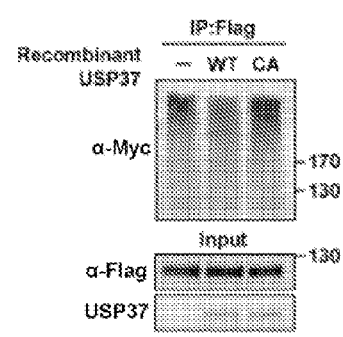

RARA deubiquitination were specific because global ubiquitination profile was not significantly changed by USP37 overexpression (FIG. 11). Accordingly, knockdown of USP37 in U937 cells increased the ubiquitination level of PLZF/RARA (FIG. 4B). We further demonstrated that the recombinant USP37 WT but not CA mutant could deubiquitinate PLZF/RARA in vitro (FIG. 4C). Along with above binding study results, these data strongly suggest that USP37 enhances PLZF/RARA protein stability by deubiquitinating PLZF/RARA.

USP37 Modulates the Cell Transformation Potential of PLZF/RARA

PLZF/RARA is able to transform hematopoietic progenitor cells by increasing capacity of cell self-renew and proliferation, and blocking the differentiation of myeloid cell lineage. Because USP37 regulates PLZF/RARA protein stability, it is conceivable that USP37 affects PLZF/RARA-mediated cell transformation of primary hematopoietic progenitor cells. To test this possible scenario, we first established the PLZF/RARA-mediated transformation using mouse primary hematopoietic progenitor cells transduced by retrovirus-expressing PLZF/RARA. As a control, PLZF/RARA transduced hematopoietic progenitor cells showed decreased expression levels of CCAAT/enhancer-binding protein family members including Cebpa, Cebpb and Cebpe, compared with cells infected with retrovirus carrying an empty vector (FIG. 5a). These results are consistent with previous reports showing suppression of CCAAT/enhancer-binding protein transcriptional factors involved in APL cells.

We next assessed the effect of Usp37 on PLZF/RARA-mediated transformation by knockdown experiments. We infected the PLZF/RARA-transduced cells with lentivirus-expressing Usp37 shRNAs. Two different Usp37 shRNAs were tested for depletion efficiency. The shUsp37#2 showed a better efficiency in downregulating Usp37 than the shUsp37#1 (FIG. 5b, left panel). As expected, depletion of Usp37 expression alleviated PLZF/RARA-associated suppression of CCAAT/enhancer-binding protein family gene expression (FIG. 5b, right panel). Consistent with the depletion efficiency, we observed that shUsp37#2-treated cells yielded higher levels of the CCAAT/enhancer-binding protein family gene expression than shUsp37#1-treated cells. These results suggest that Usp37 is important for PLZF/RARA-Mediated Cell Transformation.

To demonstrate the role of Usp37 in PLZF/RARA-elicited transformation, we further performed the methylcellulose culture of mouse primary hematopoietic progenitor cells transduced by PLZF/RARA along with or without Usp37 knockdown. As a control, hematopoietic progenitor cells infected by retrovirus carrying MSCV empty vector showed a loss of colony-formation ability after the second passage in methylcellulose culture (FIG. 5c, lanes 1 and 2). These cells expressing either shLuc or shUsp37#2 gave comparable colony number (FIG. 5c, lanes 1-4), indicating Usp37 depletion did not alter the characteristics of hematopoietic progenitors in methylcellulose culture. By contrast, PLZF/RARA-transduced cells conferred a significant increase of colony number after the second replating (lane 6). Such PLZF/RARA-mediated colony formation was significantly reduced in Usp37-depleted cells (lane 8) to an extent close to that of cells infected with control vector (lanes 2 and 4). Usp37 depletion failed to reduce PML/RARA elicited hematopoietic cells grown in methylcellulose (FIG. 12). These data suggest that the effect of Usp37 knockdown on the reduction of PLZF/RARA-induced clonogenicity is the consequence of PLZF/RARA loss.

In line with the colony-formation number, we observed that PLZF/RARA expression induced large and compact colony formation on methylcellulose culture (FIG. 5d, panels i and ii). Usp37 knockdown changed PLZF/RARA-elicited colony-formation pattern from compact and large to diffuse and smaller in size (panel ii versus iv). Furthermore, Giemsa staining showed that PLZF/RARA-transduced hematopoietic progenitor cells yielded immature cells with a feature of large nucleus and scant cytoplasm as compared with control cells (FIG. 5e, panels i and ii). Such PLZF/RARA-elicited immature cell phenotype was significantly decreased in Usp37 knockdown cells (panel iv). Accordingly, FACS analyses revealed that PLZF/RARA-transduced hematopoietic progenitor cells rendered a marked increase of the c-kit progenitor cell marker together with a reduction of myeloid differentiation markers Gr-1 and Mac-1 (FIG. 5f, panels ii and vi), compared with control cells (panels i and v). Such poor differentiation phenotypes were significantly attenuated by Usp37 knockdown (panels iv and viii). Usp37 knockdown did not significantly change the myeloid cell differentiation profiles (panels iii and vii), implying that Usp37 itself is not associated with normal hematopoietic progenitor cell differentiation into myeloid lineage. Thus, the data suggest that USP37 has an important role in regulating the protein stability and transformation capacity of PLZF/RARA in myeloid cell lineage.

Accumulating evidences indicate that DUBs are potential important targets for the treatment of human diseases, such as cancer. In this study, we have identified USP37 as a DUB for PLZF/RARA by RNAi screening. See W-C Yang and H-M Shi (2012) "The deubiquitinating enzyme USP37 regulates the oncogenic fusion protein PLZF/RARA stability" *Oncogene*, 1-9, which is incorporated herein by reference in its entirety. We demonstrate that USP37 physically interacts and modulates PLZF/RARA protein stability and further show an important role of USP37 in PLZF/RARA-mediated transformation of hematopoietic progenitor cells. Thus, our findings not only uncover a new substrate and function of USP37 but also provide a strategy in antagonizing PLZF/RARA elicited APL. Small molecules acting as ubiquitin protease inhibitors against specific DUBs have successfully been identified and proved to effectively alter cellular functions. Thus, development of small molecules inhibiting USP37 deubiquitinating activity may provide more effective and reliable clinical therapy for PLZF/RARA associated APL.

Figure 5:
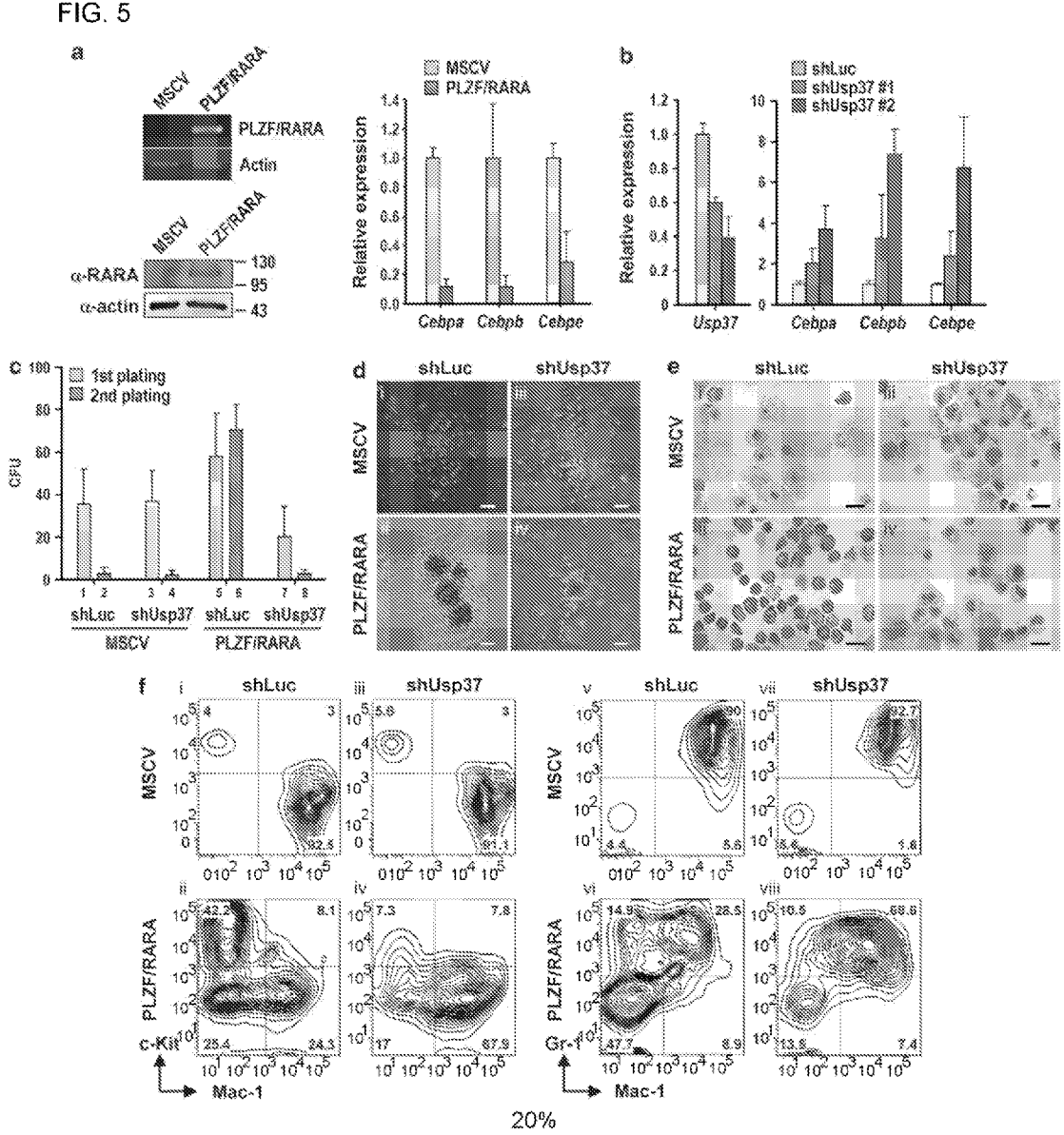
FIG. 5 shows knockdown of Usp37 attenuates PLZF/ RARA-mediated gene suppression and cell transformation. (a) Real-time qPCR analyses of endogenous Cebpa, Cebpb and Cebpe expression in mouse hematopoietic progenitor cells expressing PLZF/RARA or empty vector MSCV. Gel image and western blots show PLZF/RARA expression in retrovirus-infected mouse hematopoietic progenitor cells. Data represent the relative expression of indicated genes. Error bars are mean±s.d. from three experiments performed in duplicate. (b) Real-time qPCR analyses of endogenous Usp37, Cebpa, Cebpb and Cebpe in PLZF/RARA-transduced mouse hematopoietic progenitor cells expressing indicated shRNAs. Error bars are mean±s.d. from three experiments performed in duplicate. (c) Bar graph represents the colon) number formed from methylcellulose medium culture of mouse hematopoietic progenitor cells transduced with MSCV vector or MSCV-PLZF/RARA in combination with shLuc or shUsp37#2. Error bars indicate s.d. from three independent experiments. CFU: colony-formation unit. (d) Representative images of colonies formation from transduced mouse hematopoietic progenitor cells in methylcellulose medium at second-round replating. Bar, 200 mm. (e) Giemsa staining of indicated transduced mouse hematopoietic progenitor cells from second-round replating of methylcellulose culture. Bar, 20 mm. (f) FACS analysis of surface marker expression of indicated transduced mouse hematopoietic progenitor cells from second round replating. Data are representative of three independent experiments.

A recent study has reported that USP37 promotes the G1-S transition via regulating cyclin A stability. USP37 deubiquitinates cyclin A, causing an increased level of cyclin A to further augment cyclin A-CDK2 complex formation. Cyclin A-CDK2 then phosphorylates USP37 and enhances its deubiquitinating activity toward cyclin A, forming a positive feedback loop to promote S phase entry. Interestingly, PLZF/RARA was also shown to activate the expression of cyclin A1, an alternative CDK2 associated A-type cyclin, in human hematopoietic progenitor cells. Since cyclin A1 could form complex with CDK2 for substrate phosphorylation and also contribute to G1-S cell cycle progression in somatic cells, it is possible that PLZF/RARA-mediated transformation of hematopoietic progenitor cells is in part via activation of cyclin A1-CDK2/USP37 positive loop. In addition to causing PLZF/RARA protein destabilization, USP37 knockdown may also destroy this positive feedback loop, thus significantly reducing PLZF/RARA-mediated transformation (FIG. 5).

Besides the involvement of USP37 in PLZF/RARA-mediated cell transformation, our results that USP37 targeting to PLZF/RARA is through its N-terminal domain and PLZF moiety also implicate that USP37 may play a role in modulating PLZF protein level in a physiological context.

In addition to USP37, at least, four other DUBs, including USP2, USP29, OTUD6A, and OTUD7B, are capable of regulating PLZF/RARA level in cells (FIG. 1c). The regulation of PLZF/RARA level by these four DUBs could directly or indirectly target PLZF/RARA protein for ubiquitination. Although the distribution of USP2 and OTUD7B is not mainly localized in the nuclear compartment, we cannot exclude the possibility that both factors also play important roles for modulating PLZF/RARA protein level. Similarly, we showed that USP29 modulates PLZF/RARA protein level via RARA portion. This finding also creates an opportunity in fine tuning PLZF/RARA level in APL cells, in additional to USP37.

In summary, we demonstrate that USP37 is required for the protein stabilization and cell transformation of PLZF/RARA, thus providing USP37 as a potential target for the development of specific inhibitor in treatment of PLZF/RARA-associated APL.

All of the references cited herein are incorporated by reference in their entirety.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of assaying and/or identifying a test agent as a regulator of the stability and/or the intracellular level of the fusion protein PLZF/RARA, comprising:

(a) providing a cell comprising: (i) a first reporter protein operably linked to a tetracycline response element and the PLZF/RARA; and (ii) a second reporter protein operably linked to an internal ribosome entry site (IRES) and the PLZF/RARA, and treating the cell with the test agent or a vehicle control;

(b) inducing the cell to express the reporter proteins and measuring the intensity of the first reporter protein and the intensity of the second reporter protein, and calculating the ratio of the intensity of the first reporter protein versus the intensity of the second reporter protein in the presence and the absence of the test agent; and (c) identifying the test agent as a positive regulator of the stability and/or the level of the fusion protein PLZF/RARA when the ratio in the presence of the test agent is less than that in the vehicle control, or a negative regulator of the stability and/or the level of the fusion protein PLZF/RARA when the ratio in the presence of the test agent is greater than that in the vehicle control; or
(i) providing a cell constitutively expressing a transduced fusion protein PLZF/RARA and a transduced USP37, and treating the cell with the test agent or a vehicle control;
(ii) measuring the amount of the PLZF/RARA in the presence and the absence of the test agent; and
(iii) identifying the test agent as a negative regulator of the stability and/or the level of the fusion protein PLZF/RARA when the amount of the PLZF/RARA in the presence of the test agent is less than that in the vehicle control, or a positive regulator of the stability and/or the level of the fusion protein PLZF/RARA when the amount of the PLZF/RARA in the presence of the test agent is more than that in the vehicle control; or
(1) providing a cell constitutively expressing a transduced fusion protein PLZF/RARA and a transduced USP37, and treating the cell with a proteasome inhibitor, which reduces the degradation of ubiquitin-conjugated proteins, and the test agent or a vehicle control;
(2) measuring the amount of ubiquitin-conjugated PLZF/RARA within the cell in the presence and the absence of the test agent; and
(3) identifying the test agent as a positive regulator of the stability and/or the level of the fusion protein PLZF/RARA when the amount of the ubiquitin-conjugated PLZF/RARA in the presence of the test agent is more than that in the vehicle control, or a negative regulator of the stability and/or the level of the fusion protein PLZF/RARA when the amount of the ubiquitin-conjugated PLZF/RARA in the presence of the test agent is less than that in the vehicle control.

2. The method of claim 1, wherein step (c) further comprises:
(d) inhibiting the biosynthesis of the PLZF/RARA;
(e) measuring the amounts of the PLZF/RARA at different time intervals to obtain the half-life of the PLZF/RARA in the presence and the absence of the test agent; and
(f) validating the test agent as a regulator of the stability and/or the level of the fusion protein PLZF/RARA when the half-life of the PLZF/RARA in the presence of the test agent is shorter than that in the vehicle control.

3. The method of claim 2, wherein step (d) is performed in the presence of cycloheximide.

4. The method of claim 1, wherein the proteasome inhibitor in step (1) is MG132.

5. The method of claim 1, further comprising:
a) causing a depletion of USP37 transcripts within the cell;
b) assessing the impact of the depletion of the USP37 transcripts within the cell on the effect of the test agent identified; and
c) validating the test agent identified as a USP37-dependent regulator of the stability and/or the level of the fusion protein PLZF/RARA when the effect of the test agent is diminished or lost.

6. The method of claim 5, wherein step b) assessing the impact of the depletion of the USP37 transcripts on the effect of the test agent in decreasing the ratio of the intensity of the first reporter protein versus the intensity of the second reporter protein.

7. The method of claim 1, wherein the test agent is at least one selected from the group consisting of a small interfering RNA (siRNA) molecule, a small hairpin RNA (shRNA) molecule, an antisense molecule, and a small organic molecule.

8. The method of claim 1, further comprising:
I) contacting a human ubiquitin specific peptidase 37 (USP37) with the test agent identified; and
II) measuring the human USP37 for ubiquitin hydrolase activity in the presence and the absence of the test agent to validate the test agent identified as a potential inhibitor that inhibits the activity of the USP37.

9. The method of claim 1, further evaluating the test agent identified as a potential therapeutic agent for treating PLZF/RARA-associated acute promyelocytic leukemia (APL).

10. The method of claim 9, wherein the evaluating step is performed by measuring the potency of the test agent identified in inhibiting colony formation and/or proliferation of PLZF/RARA-transduced and/or PLZF/RARA-expressing hematopoietic progenitor cells.

11. The method of claim 1, further comprising:
assessing the test agent identified for activity in inhibiting the transcript expression level of USP37.

12. The method of claim 1, wherein the cell is at least one selected from the group consisting of U937, HL60, HEK-293T cell line, a HeLa cell line, and a human primary hematopoietic cell.

* * * * *

SEQUENCE LISTING

```
<160> NUMBER OF SEQ ID NOS: 59

<210> SEQ ID NO 1
<211> LENGTH: 21
<212> TYPE: DNA
<213> ORGANISM: Artificial Sequence
<220> FEATURE:
<223> OTHER INFORMATION: shUsp37 #1

<400> SEQUENCE: 1
cgcctaatgt tgactttaca a                                      21

<210> SEQ ID NO 2
<211> LENGTH: 21
<212> TYPE: DNA
<213> ORGANISM: Artificial Sequence
<220> FEATURE:
<223> OTHER INFORMATION: shUsp37 #2

<400> SEQUENCE: 2
gcagaagatg atattccaga a                                      21

<210> SEQ ID NO 3
<211> LENGTH: 18
<212> TYPE: DNA
<213> ORGANISM: Artificial Sequence
<220> FEATURE:
<223> OTHER INFORMATION: Cebpa forward primer

<400> SEQUENCE: 3
aggaacttga agcacaat                                          18

<210> SEQ ID NO 4
<211> LENGTH: 18
<212> TYPE: DNA
<213> ORGANISM: Artificial Sequence
<220> FEATURE:
<223> OTHER INFORMATION: Cebpa reverse primer

<400> SEQUENCE: 4
```

```
acacagagac cagataca                                                    18

<210> SEQ ID NO 5
<211> LENGTH: 18
<212> TYPE: DNA
<213> ORGANISM: Artificial Sequence
<220> FEATURE:
<223> OTHER INFORMATION: Cebpb forward primer

<400> SEQUENCE: 5
cggggttgtt gatgtttt                                                    18

<210> SEQ ID NO 6
<211> LENGTH: 21
<212> TYPE: DNA
<213> ORGANISM: Artificial Sequence
<220> FEATURE:
<223> OTHER INFORMATION: Cebpb reverse primer

<400> SEQUENCE: 6
catacgcctc ttttctcata g                                                21

<210> SEQ ID NO 7
<211> LENGTH: 18
<212> TYPE: DNA
<213> ORGANISM: Artificial Sequence
<220> FEATURE:
<223> OTHER INFORMATION: Cebpe forward primer

<400> SEQUENCE: 7
caagaaggca gtgaacaa                                                    18

<210> SEQ ID NO 8
<211> LENGTH: 18
<212> TYPE: DNA
<213> ORGANISM: Artificial Sequence
<220> FEATURE:
<223> OTHER INFORMATION: Cebpe reverse primer

<400> SEQUENCE: 8
gctgagtctc cataatgc                                                    18

<210> SEQ ID NO 9
<211> LENGTH: 18
<212> TYPE: DNA
<213> ORGANISM: Artificial Sequence
<220> FEATURE:
<223> OTHER INFORMATION: Usp37 forward primer

<400> SEQUENCE: 9
ctcatcagtg ttgtcagt                                                    18

<210> SEQ ID NO 10
<211> LENGTH: 18
<212> TYPE: DNA
<213> ORGANISM: Artificial Sequence
<220> FEATURE:
<223> OTHER INFORMATION: Usp37 reverse primer

<400> SEQUENCE: 10
tccaggtcat tgtaagtg                                                    18

<210> SEQ ID NO 11
<211> LENGTH: 23
<212> TYPE: DNA
```

```
<213> ORGANISM: Artificial Sequence
<220> FEATURE:
<223> OTHER INFORMATION: Hprt forward primer

<400> SEQUENCE: 11
gattagcgat gatgaaccag gtt                                          23

<210> SEQ ID NO 12
<211> LENGTH: 21
<212> TYPE: DNA
<213> ORGANISM: Artificial Sequence
<220> FEATURE:
<223> OTHER INFORMATION: Hprt reverse primer

<400> SEQUENCE: 12
cctcccatct ccttcatgac a                                            21

<210> SEQ ID NO 13
<211> LENGTH: 20
<212> TYPE: DNA
<213> ORGANISM: Artificial Sequence
<220> FEATURE:
<223> OTHER INFORMATION: PLZF/RARA forward primer

<400> SEQUENCE: 13
tgaagacgta cgggtgcgag                                              20

<210> SEQ ID NO 14
<211> LENGTH: 20
<212> TYPE: DNA
<213> ORGANISM: Artificial Sequence
<220> FEATURE:
<223> OTHER INFORMATION: PLZF/RARA reverse primer

<400> SEQUENCE: 14
tgtagatgcg gggtagaggg                                              20

<210> SEQ ID NO 15
<211> LENGTH: 20
<212> TYPE: DNA
<213> ORGANISM: Artificial Sequence
<220> FEATURE:
<223> OTHER INFORMATION: actin forward primer

<400> SEQUENCE: 15
cctagaagca tttgcggtgg                                              20

<210> SEQ ID NO 16
<211> LENGTH: 20
<212> TYPE: DNA
<213> ORGANISM: Artificial Sequence
<220> FEATURE:
<223> OTHER INFORMATION: actin reverse primer

<400> SEQUENCE: 16
gagctacgag ctgcctgacg                                              20

<210> SEQ ID NO 17
<211> LENGTH: 979
<212> TYPE: PRT
<213> ORGANISM: Homo sapiens

<400> SEQUENCE: 17

Met Ser Pro Leu Lys Ile His Gly Pro Ile Arg Ile Arg Ser Met Gln
1               5                   10                  15
```

Thr Gly Ile Thr Lys Trp Lys Glu Gly Ser Phe Glu Ile Val Glu Lys
            20                  25                  30

Glu Asn Lys Val Ser Leu Val Val His Tyr Asn Thr Gly Gly Ile Pro
        35                  40                  45

Arg Ile Phe Gln Leu Ser His Asn Ile Lys Asn Val Val Leu Arg Pro
    50                  55                  60

Ser Gly Ala Lys Gln Ser Arg Leu Met Leu Thr Leu Gln Asp Asn Ser
65                  70                  75                  80

Phe Leu Ser Ile Asp Lys Val Pro Ser Lys Asp Ala Glu Glu Met Arg
                85                  90                  95

Leu Phe Leu Asp Ala Val His Gln Asn Arg Leu Pro Ala Ala Met Lys
            100                 105                 110

Pro Ser Gln Gly Ser Gly Ser Phe Gly Ala Ile Leu Gly Ser Arg Thr
        115                 120                 125

Ser Gln Lys Glu Thr Ser Arg Gln Leu Ser Tyr Ser Asp Asn Gln Ala
    130                 135                 140

Ser Ala Lys Arg Gly Ser Leu Glu Thr Lys Asp Asp Ile Pro Phe Arg
145                 150                 155                 160

Lys Val Leu Gly Asn Pro Gly Arg Gly Ser Ile Lys Thr Val Ala Gly
                165                 170                 175

Ser Gly Ile Ala Arg Thr Ile Pro Ser Leu Thr Ser Thr Ser Thr Pro
            180                 185                 190

Leu Arg Ser Gly Leu Leu Glu Asn Arg Thr Glu Lys Arg Lys Arg Met
        195                 200                 205

Ile Ser Thr Gly Ser Glu Leu Asn Glu Asp Tyr Pro Lys Glu Asn Asp
    210                 215                 220

Ser Ser Ser Asn Asn Lys Ala Met Thr Asp Pro Ser Arg Lys Tyr Leu
225                 230                 235                 240

Thr Ser Ser Arg Glu Lys Gln Leu Ser Leu Lys Gln Ser Glu Glu Asn
                245                 250                 255

Arg Thr Ser Gly Leu Leu Pro Leu Gln Ser Ser Phe Tyr Gly Ser
            260                 265                 270

Arg Ala Gly Ser Lys Glu His Ser Ser Gly Gly Thr Asn Leu Asp Arg
        275                 280                 285

Thr Asn Val Ser Ser Gln Thr Pro Ser Ala Lys Arg Ser Leu Gly Phe
    290                 295                 300

Leu Pro Gln Pro Val Pro Leu Ser Val Lys Lys Leu Arg Cys Asn Gln
305                 310                 315                 320

Asp Tyr Thr Gly Trp Asn Lys Pro Arg Val Pro Leu Ser Ser His Gln
                325                 330                 335

Gln Gln Gln Leu Gln Gly Phe Ser Asn Leu Gly Asn Thr Cys Tyr Met
            340                 345                 350

Asn Ala Ile Leu Gln Ser Leu Phe Ser Leu Gln Ser Phe Ala Asn Asp
        355                 360                 365

Leu Leu Lys Gln Gly Ile Pro Trp Lys Lys Ile Pro Leu Asn Ala Leu
    370                 375                 380

Ile Arg Arg Phe Ala His Leu Leu Val Lys Lys Asp Ile Cys Asn Ser
385                 390                 395                 400

Glu Thr Lys Lys Asp Leu Leu Lys Lys Val Lys Asn Ala Ile Ser Ala
                405                 410                 415

Thr Ala Glu Arg Phe Ser Gly Tyr Met Gln Asn Asp Ala His Glu Phe
            420                 425                 430

Leu Ser Gln Cys Leu Asp Gln Leu Lys Glu Asp Met Glu Lys Leu Asn

-continued

```
            435                 440                 445
Lys Thr Trp Lys Thr Glu Pro Val Ser Gly Glu Asn Ser Pro Asp
450                 455                 460
Ile Ser Ala Thr Arg Ala Tyr Thr Cys Pro Val Ile Thr Asn Leu Glu
465                 470                 475                 480
Phe Glu Val Gln His Ser Ile Ile Cys Lys Ala Cys Gly Glu Ile Ile
                        485                 490                 495
Pro Lys Arg Glu Gln Phe Asn Asp Leu Ser Ile Asp Leu Pro Arg Arg
                500                 505                 510
Lys Lys Pro Leu Pro Arg Ser Ile Gln Asp Ser Leu Asp Leu Phe
                515                 520                 525
Phe Arg Ala Glu Glu Leu Glu Tyr Ser Cys Glu Lys Cys Gly Gly Lys
            530                 535                 540
Cys Ala Leu Val Arg His Lys Phe Asn Arg Leu Pro Arg Val Leu Ile
545                 550                 555                 560
Leu His Leu Lys Arg Tyr Ser Phe Asn Val Ala Leu Ser Leu Asn Asn
                            565                 570                 575
Lys Ile Gly Gln Gln Val Ile Ile Pro Arg Tyr Leu Thr Leu Ser Ser
                580                 585                 590
His Cys Thr Glu Asn Thr Lys Pro Pro Phe Thr Leu Gly Trp Ser Ala
                595                 600                 605
His Met Ala Ile Ser Arg Pro Leu Lys Ala Ser Gln Met Val Asn Ser
610                 615                 620
Cys Ile Thr Ser Pro Ser Thr Pro Ser Lys Lys Phe Thr Phe Lys Ser
625                 630                 635                 640
Lys Ser Ser Leu Ala Leu Cys Leu Asp Ser Asp Ser Glu Asp Glu Leu
                        645                 650                 655
Lys Arg Ser Val Ala Leu Ser Gln Arg Leu Cys Glu Met Leu Gly Asn
                660                 665                 670
Glu Gln Gln Gln Glu Asp Leu Glu Lys Asp Ser Lys Leu Cys Pro Ile
                675                 680                 685
Glu Pro Asp Lys Ser Glu Leu Glu Asn Ser Gly Phe Asp Arg Met Ser
            690                 695                 700
Glu Glu Glu Leu Leu Ala Ala Val Leu Glu Ile Ser Lys Arg Asp Ala
705                 710                 715                 720
Ser Pro Ser Leu Ser His Glu Asp Asp Lys Pro Thr Ser Ser Pro
                    725                 730                 735
Asp Thr Gly Phe Ala Glu Asp Ile Gln Glu Met Pro Glu Asn Pro
                    740                 745                 750
Asp Thr Met Glu Thr Glu Lys Pro Lys Thr Ile Thr Glu Leu Asp Pro
            755                 760                 765
Ala Ser Phe Thr Glu Ile Thr Lys Asp Cys Asp Glu Asn Lys Glu Asn
                770                 775                 780
Lys Thr Pro Glu Gly Ser Gln Gly Glu Val Asp Trp Leu Gln Gln Tyr
785                 790                 795                 800
Asp Met Glu Arg Glu Arg Glu Glu Glu Leu Gln Gln Ala Leu Ala
                        805                 810                 815
Gln Ser Leu Gln Glu Gln Glu Ala Trp Glu Gln Lys Glu Asp Asp Asp
                820                 825                 830
Leu Lys Arg Ala Thr Glu Leu Ser Leu Gln Glu Phe Asn Asn Ser Phe
            835                 840                 845
Val Asp Ala Leu Gly Ser Asp Glu Asp Ser Gly Asn Glu Asp Val Phe
            850                 855                 860
```

```
Asp Met Glu Tyr Thr Glu Ala Glu Ala Glu Leu Lys Arg Asn Ala
865                 870                 875                 880

Glu Thr Gly Asn Leu Pro His Ser Tyr Arg Leu Ile Ser Val Val Ser
            885                 890                 895

His Ile Gly Ser Thr Ser Ser Gly His Tyr Ile Ser Asp Val Tyr
            900                 905                 910

Asp Ile Lys Lys Gln Ala Trp Phe Thr Tyr Asn Asp Leu Glu Val Ser
            915                 920                 925

Lys Ile Gln Glu Ala Ala Val Gln Ser Asp Arg Asp Arg Ser Gly Tyr
            930                 935                 940

Ile Phe Phe Tyr Met His Lys Glu Ile Phe Asp Glu Leu Leu Glu Thr
945                 950                 955                 960

Glu Lys Asn Ser Gln Ser Leu Ser Thr Glu Val Gly Lys Thr Thr Arg
                965                 970                 975

Gln Ala Leu

<210> SEQ ID NO 18
<211> LENGTH: 922
<212> TYPE: PRT
<213> ORGANISM: Homo sapiens

<400> SEQUENCE: 18

Met Ile Ser Leu Lys Val Cys Gly Phe Ile Gln Ile Trp Ser Gln Lys
1               5                   10                  15

Thr Gly Met Thr Lys Leu Lys Glu Ala Leu Ile Glu Thr Val Gln Arg
                20                  25                  30

Gln Lys Glu Ile Lys Leu Val Val Thr Phe Lys Ser Gly Lys Phe Ile
            35                  40                  45

Arg Ile Phe Gln Leu Ser Asn Asn Ile Arg Ser Val Val Leu Arg His
        50                  55                  60

Cys Lys Lys Arg Gln Ser His Leu Arg Leu Thr Leu Lys Asn Asn Val
65                  70                  75                  80

Phe Leu Phe Ile Asp Lys Leu Ser Tyr Arg Asp Ala Lys Gln Leu Asn
                85                  90                  95

Met Phe Leu Asp Ile Ile His Gln Asn Lys Ser Gln Gln Pro Met Lys
                100                 105                 110

Ser Asp Asp Asp Trp Ser Val Phe Glu Ser Arg Asn Met Leu Lys Glu
            115                 120                 125

Ile Asp Lys Thr Ser Phe Tyr Ser Ile Cys Asn Lys Pro Ser Tyr Gln
        130                 135                 140

Lys Met Pro Leu Phe Met Ser Lys Ser Pro Thr His Val Lys Lys Gly
145                 150                 155                 160

Ile Leu Glu Asn Gln Gly Gly Lys Gly Gln Asn Thr Leu Ser Ser Asp
                165                 170                 175

Val Gln Thr Asn Glu Asp Ile Leu Lys Glu Asp Asn Pro Val Pro Asn
            180                 185                 190

Lys Lys Tyr Lys Thr Asp Ser Leu Lys Tyr Ile Gln Ser Asn Arg Lys
        195                 200                 205

Asn Pro Ser Ser Leu Glu Asp Leu Glu Lys Asp Arg Asp Leu Lys Leu
    210                 215                 220

Gly Pro Ser Phe Asn Thr Asn Cys Asn Gly Asn Pro Asn Leu Asp Glu
225                 230                 235                 240

Thr Val Leu Ala Thr Gln Thr Leu Asn Ala Lys Asn Gly Leu Thr Ser
                245                 250                 255
```

```
Pro Leu Glu Pro Glu His Ser Gln Gly Asp Pro Arg Cys Asn Lys Ala
            260                 265                 270

Gln Val Pro Leu Asp Ser His Ser Gln Leu Gln Gln Gly Phe Pro
        275                 280                 285

Asn Leu Gly Asn Thr Cys Tyr Met Asn Ala Val Leu Gln Ser Leu Phe
        290                 295                 300

Ala Ile Pro Ser Phe Ala Asp Asp Leu Leu Thr Gln Gly Val Pro Trp
305                 310                 315                 320

Glu Tyr Ile Pro Phe Glu Ala Leu Ile Met Thr Leu Thr Gln Leu Leu
                325                 330                 335

Ala Leu Lys Asp Phe Cys Ser Thr Lys Ile Lys Arg Glu Leu Leu Gly
            340                 345                 350

Asn Val Lys Lys Val Ile Ser Ala Val Ala Glu Ile Phe Ser Gly Asn
        355                 360                 365

Met Gln Asn Asp Ala His Glu Phe Leu Gly Gln Cys Leu Asp Gln Leu
    370                 375                 380

Lys Glu Asp Met Glu Lys Leu Asn Ala Thr Leu Asn Thr Gly Lys Glu
385                 390                 395                 400

Cys Gly Asp Glu Asn Ser Ser Pro Gln Met His Val Gly Ser Ala Ala
                405                 410                 415

Thr Lys Val Phe Val Cys Pro Val Val Ala Asn Phe Glu Phe Glu Leu
            420                 425                 430

Gln Leu Ser Leu Ile Cys Lys Ala Cys Gly His Ala Val Leu Lys Val
        435                 440                 445

Glu Pro Asn Asn Tyr Leu Ser Ile Asn Leu His Gln Glu Thr Lys Pro
        450                 455                 460

Leu Pro Leu Ser Ile Gln Asn Ser Leu Asp Leu Phe Phe Lys Glu Glu
465                 470                 475                 480

Glu Leu Glu Tyr Asn Cys Gln Met Cys Lys Gln Lys Ser Cys Val Ala
                485                 490                 495

Arg His Thr Phe Ser Arg Leu Ser Arg Val Leu Ile Ile His Leu Lys
            500                 505                 510

Arg Tyr Ser Phe Asn Asn Ala Trp Leu Leu Val Lys Asn Asn Glu Gln
        515                 520                 525

Val Tyr Ile Pro Lys Ser Leu Ser Leu Ser Ser Tyr Cys Asn Glu Ser
        530                 535                 540

Thr Lys Pro Pro Leu Pro Leu Ser Ser Ser Ala Pro Val Gly Lys Cys
545                 550                 555                 560

Glu Val Leu Glu Val Ser Gln Glu Met Ile Ser Glu Ile Asn Ser Pro
                565                 570                 575

Leu Thr Pro Ser Met Lys Leu Thr Ser Glu Ser Ser Asp Ser Leu Val
            580                 585                 590

Leu Pro Val Glu Pro Asp Lys Asn Ala Asp Leu Gln Arg Phe Gln Arg
        595                 600                 605

Asp Cys Gly Asp Ala Ser Gln Glu Gln His Gln Arg Asp Leu Glu Asn
        610                 615                 620

Gly Ser Ala Leu Glu Ser Glu Leu Val His Phe Arg Asp Arg Ala Ile
625                 630                 635                 640

Gly Glu Lys Glu Leu Pro Val Ala Asp Ser Leu Met Asp Gln Gly Asp
                645                 650                 655

Ile Ser Leu Pro Val Met Tyr Glu Asp Gly Gly Lys Leu Ile Ser Ser
            660                 665                 670
```

```
Pro Asp Thr Arg Leu Val Glu Val His Leu Gln Glu Val Pro Gln His
            675                 680                 685

Pro Glu Leu Gln Lys Tyr Glu Lys Thr Asn Thr Phe Val Glu Phe Asn
        690                 695                 700

Phe Asp Ser Val Thr Glu Ser Thr Asn Gly Phe Tyr Asp Cys Lys Glu
705                 710                 715                 720

Asn Arg Ile Pro Glu Gly Ser Gln Gly Met Ala Glu Gln Leu Gln Gln
                725                 730                 735

Cys Ile Glu Glu Ser Ile Ile Asp Glu Phe Leu Gln Gln Ala Pro Pro
            740                 745                 750

Pro Gly Val Arg Lys Leu Asp Ala Gln Glu His Thr Glu Glu Thr Leu
        755                 760                 765

Asn Gln Ser Thr Glu Leu Arg Leu Gln Lys Ala Asp Leu Asn His Leu
    770                 775                 780

Gly Ala Leu Gly Ser Asp Asn Pro Gly Asn Lys Asn Ile Leu Asp Ala
785                 790                 795                 800

Glu Asn Thr Arg Gly Glu Ala Lys Glu Leu Thr Arg Asn Val Lys Met
                805                 810                 815

Gly Asp Pro Leu Gln Ala Tyr Arg Leu Ile Ser Val Val Ser His Ile
            820                 825                 830

Gly Ser Ser Pro Asn Ser Gly His Tyr Ile Ser Asp Val Tyr Asp Phe
        835                 840                 845

Gln Lys Gln Ala Trp Phe Thr Tyr Asn Asp Leu Cys Val Ser Glu Ile
    850                 855                 860

Ser Glu Thr Lys Met Gln Glu Ala Arg Leu His Ser Gly Tyr Ile Phe
865                 870                 875                 880

Phe Tyr Met His Asn Gly Ile Phe Glu Glu Leu Leu Arg Lys Ala Glu
                885                 890                 895

Asn Ser Arg Leu Pro Ser Thr Gln Ala Gly Val Ile Pro Gln Gly Glu
            900                 905                 910

Tyr Glu Gly Asp Ser Leu Tyr Arg Pro Ala
        915                 920

<210> SEQ ID NO 19
<211> LENGTH: 843
<212> TYPE: PRT
<213> ORGANISM: Homo sapiens

<400> SEQUENCE: 19

Met Thr Leu Asp Met Asp Ala Val Leu Ser Asp Phe Val Arg Ser Thr
1               5                   10                  15

Gly Ala Glu Pro Gly Leu Ala Arg Asp Leu Leu Glu Gly Lys Asn Trp
            20                  25                  30

Asp Val Asn Ala Ala Leu Ser Asp Phe Glu Gln Leu Arg Gln Val His
        35                  40                  45

Ala Gly Asn Leu Pro Pro Ser Phe Ser Glu Gly Ser Gly Gly Ser Arg
    50                  55                  60

Thr Pro Glu Lys Gly Phe Ser Asp Arg Glu Pro Thr Arg Pro Pro Arg
65                  70                  75                  80

Pro Ile Leu Gln Arg Gln Asp Asp Ile Val Gln Glu Lys Arg Leu Ser
                85                  90                  95

Arg Gly Ile Ser His Ala Ser Ser Ile Val Ser Leu Ala Arg Ser
            100                 105                 110

His Val Ser Ser Asn Gly Gly Gly Gly Ser Asn Glu His Pro Leu
        115                 120                 125
```

```
Glu Met Pro Ile Cys Ala Phe Gln Leu Pro Asp Leu Thr Val Tyr Asn
    130                 135                 140

Glu Asp Phe Arg Ser Phe Ile Glu Arg Asp Leu Ile Glu Gln Ser Met
145                 150                 155                 160

Leu Val Ala Leu Glu Gln Ala Gly Arg Leu Asn Trp Trp Val Ser Val
                165                 170                 175

Asp Pro Thr Ser Gln Arg Leu Leu Pro Leu Ala Thr Thr Gly Asp Gly
            180                 185                 190

Asn Cys Leu Leu His Ala Ala Ser Leu Gly Met Trp Gly Phe His Asp
        195                 200                 205

Arg Asp Leu Met Leu Arg Lys Ala Leu Tyr Ala Leu Met Glu Lys Gly
    210                 215                 220

Val Glu Lys Glu Ala Leu Lys Arg Arg Trp Arg Trp Gln Gln Thr Gln
225                 230                 235                 240

Gln Asn Lys Glu Ser Gly Leu Val Tyr Thr Glu Asp Glu Trp Gln Lys
                245                 250                 255

Glu Trp Asn Glu Leu Ile Lys Leu Ala Ser Ser Glu Pro Arg Met His
            260                 265                 270

Leu Gly Thr Asn Gly Ala Asn Cys Gly Gly Val Glu Ser Ser Glu Glu
        275                 280                 285

Pro Val Tyr Glu Ser Leu Glu Glu Phe His Val Phe Val Leu Ala His
    290                 295                 300

Val Leu Arg Arg Pro Ile Val Val Ala Asp Thr Met Leu Arg Asp
305                 310                 315                 320

Ser Gly Gly Glu Ala Phe Ala Pro Ile Pro Phe Gly Gly Ile Tyr Leu
                325                 330                 335

Pro Leu Glu Val Pro Ala Ser Gln Cys His Arg Ser Pro Leu Val Leu
            340                 345                 350

Ala Tyr Asp Gln Ala His Phe Ser Ala Leu Val Ser Met Glu Gln Lys
        355                 360                 365

Glu Asn Thr Lys Glu Gln Ala Val Ile Pro Leu Thr Asp Ser Glu Tyr
    370                 375                 380

Lys Leu Leu Pro Leu His Phe Ala Val Asp Pro Gly Lys Gly Trp Glu
385                 390                 395                 400

Trp Gly Lys Asp Asp Ser Asp Asn Val Arg Leu Ala Ser Val Ile Leu
                405                 410                 415

Ser Leu Glu Val Lys Leu His Leu Leu His Ser Tyr Met Asn Val Lys
            420                 425                 430

Trp Ile Pro Leu Ser Ser Asp Ala Gln Ala Pro Leu Ala Gln Pro Glu
        435                 440                 445

Ser Pro Thr Ala Ser Ala Gly Asp Glu Pro Arg Ser Thr Pro Glu Ser
    450                 455                 460

Gly Asp Ser Asp Lys Glu Ser Val Gly Ser Ser Thr Ser Asn Glu
465                 470                 475                 480

Gly Gly Arg Arg Lys Glu Lys Ser Lys Arg Asp Arg Glu Lys Asp Lys
                485                 490                 495

Lys Arg Ala Asp Ser Val Ala Asn Lys Leu Gly Ser Phe Gly Lys Thr
            500                 505                 510

Leu Gly Ser Lys Leu Lys Lys Asn Met Gly Gly Leu Met His Ser Lys
        515                 520                 525

Gly Ser Lys Pro Gly Gly Val Gly Thr Gly Leu Gly Gly Ser Ser Gly
    530                 535                 540
```

-continued

```
Thr Glu Thr Leu Glu Lys Lys Lys Asn Ser Leu Lys Ser Trp Lys
545                 550                 555                 560

Gly Gly Lys Glu Glu Ala Ala Gly Asp Gly Pro Val Ser Glu Lys Pro
                565                 570                 575

Pro Ala Glu Ser Val Gly Asn Gly Gly Ser Lys Tyr Ser Gln Glu Val
            580                 585                 590

Met Gln Ser Leu Ser Ile Leu Arg Thr Ala Met Gln Gly Glu Gly Lys
        595                 600                 605

Phe Ile Phe Val Gly Thr Leu Lys Met Gly His Arg His Gln Tyr Gln
    610                 615                 620

Glu Glu Met Ile Gln Arg Tyr Leu Ser Asp Ala Glu Glu Arg Phe Leu
625                 630                 635                 640

Ala Glu Gln Lys Gln Lys Glu Ala Glu Arg Lys Ile Met Asn Gly Gly
                645                 650                 655

Ile Gly Gly Gly Pro Pro Ala Lys Lys Pro Glu Pro Asp Ala Arg
            660                 665                 670

Glu Glu Gln Pro Thr Gly Pro Pro Ala Glu Ser Arg Ala Met Ala Phe
        675                 680                 685

Ser Thr Gly Tyr Pro Gly Asp Phe Thr Ile Pro Arg Pro Ser Gly Gly
    690                 695                 700

Gly Val His Cys Gln Glu Pro Arg Arg Gln Leu Ala Gly Gly Pro Cys
705                 710                 715                 720

Val Gly Gly Leu Pro Pro Tyr Ala Thr Phe Pro Arg Gln Cys Pro Pro
                725                 730                 735

Gly Arg Pro Tyr Pro His Gln Asp Ser Ile Pro Ser Leu Glu Pro Gly
            740                 745                 750

Ser His Ser Lys Asp Gly Leu His Arg Gly Ala Leu Leu Pro Pro Pro
        755                 760                 765

Tyr Arg Val Ala Asp Ser Tyr Ser Asn Gly Tyr Arg Glu Pro Pro Glu
    770                 775                 780

Pro Asp Gly Trp Ala Gly Gly Leu Arg Gly Leu Pro Pro Thr Gln Thr
785                 790                 795                 800

Lys Cys Lys Gln Pro Asn Cys Ser Phe Tyr Gly His Pro Glu Thr Asn
                805                 810                 815

Asn Phe Cys Ser Cys Cys Tyr Arg Glu Glu Leu Arg Arg Arg Glu Arg
            820                 825                 830

Glu Pro Asp Gly Glu Leu Leu Val His Arg Phe
        835                 840

<210> SEQ ID NO 20
<211> LENGTH: 21
<212> TYPE: DNA
<213> ORGANISM: Artificial Sequence
<220> FEATURE:
<223> OTHER INFORMATION: MPND shRNA clone 1

<400> SEQUENCE: 20
ctttgcagcc atcaacaagt t                                            21

<210> SEQ ID NO 21
<211> LENGTH: 21
<212> TYPE: DNA
<213> ORGANISM: Artificial Sequence
<220> FEATURE:
<223> OTHER INFORMATION: MPND shRNA clone 2

<400> SEQUENCE: 21
```

```
ctggtggaag taacatcctt t                                              21
```

<210> SEQ ID NO 22
<211> LENGTH: 21
<212> TYPE: DNA
<213> ORGANISM: Artificial Sequence
<220> FEATURE:
<223> OTHER INFORMATION: MPND shRNA clone 3

<400> SEQUENCE: 22

```
gccagaaact ggacaagtac a                                              21
```

<210> SEQ ID NO 23
<211> LENGTH: 21
<212> TYPE: DNA
<213> ORGANISM: Artificial Sequence
<220> FEATURE:
<223> OTHER INFORMATION: MPND shRNA clone 4

<400> SEQUENCE: 23

```
ctctgtcaag tacaaaggcc a                                              21
```

<210> SEQ ID NO 24
<211> LENGTH: 21
<212> TYPE: DNA
<213> ORGANISM: Artificial Sequence
<220> FEATURE:
<223> OTHER INFORMATION: MPND shRNA clone 5

<400> SEQUENCE: 24

```
cgttcaacgt ggctgtttct a                                              21
```

<210> SEQ ID NO 25
<211> LENGTH: 21
<212> TYPE: DNA
<213> ORGANISM: Artificial Sequence
<220> FEATURE:
<223> OTHER INFORMATION: OTUD5 shRNA clone 1

<400> SEQUENCE: 25

```
ccatcattca aaccagggtt t                                              21
```

<210> SEQ ID NO 26
<211> LENGTH: 21
<212> TYPE: DNA
<213> ORGANISM: Artificial Sequence
<220> FEATURE:
<223> OTHER INFORMATION: OTUD5 shRNA clone 2

<400> SEQUENCE: 26

```
ctgaccttgc tgcattcctt t                                              21
```

<210> SEQ ID NO 27
<211> LENGTH: 21
<212> TYPE: DNA
<213> ORGANISM: Artificial Sequence
<220> FEATURE:
<223> OTHER INFORMATION: OTUD5 shRNA clone 3

<400> SEQUENCE: 27

```
gcatgctgaa ttgggcatga a                                              21
```

<210> SEQ ID NO 28
<211> LENGTH: 21
<212> TYPE: DNA
<213> ORGANISM: Artificial Sequence

```
<220> FEATURE:
<223> OTHER INFORMATION: OTUD5 shRNA clone 4

<400> SEQUENCE: 28
caacaggaat acctagacag t                                              21

<210> SEQ ID NO 29
<211> LENGTH: 21
<212> TYPE: DNA
<213> ORGANISM: Artificial Sequence
<220> FEATURE:
<223> OTHER INFORMATION: OTUD5 shRNA clone 5

<400> SEQUENCE: 29
cactagcttc tttggaatct t                                              21

<210> SEQ ID NO 30
<211> LENGTH: 21
<212> TYPE: DNA
<213> ORGANISM: Artificial Sequence
<220> FEATURE:
<223> OTHER INFORMATION: OTUD6A shRNA clone 1

<400> SEQUENCE: 30
gaaacgaaat tcgagggaaa t                                              21

<210> SEQ ID NO 31
<211> LENGTH: 21
<212> TYPE: DNA
<213> ORGANISM: Artificial Sequence
<220> FEATURE:
<223> OTHER INFORMATION: OTUD6A shRNA clone 2

<400> SEQUENCE: 31
catgatctac tgcgacaaca t                                              21

<210> SEQ ID NO 32
<211> LENGTH: 21
<212> TYPE: DNA
<213> ORGANISM: Artificial Sequence
<220> FEATURE:
<223> OTHER INFORMATION: OTUD6A shRNA clone 3

<400> SEQUENCE: 32
cgacagtagc attgaatctg t                                              21

<210> SEQ ID NO 33
<211> LENGTH: 21
<212> TYPE: DNA
<213> ORGANISM: Artificial Sequence
<220> FEATURE:
<223> OTHER INFORMATION: OTUD6A shRNA clone 4

<400> SEQUENCE: 33
caccaactaa gatttggtca t                                              21

<210> SEQ ID NO 34
<211> LENGTH: 21
<212> TYPE: DNA
<213> ORGANISM: Artificial Sequence
<220> FEATURE:
<223> OTHER INFORMATION: OTUD6B shRNA clone 1

<400> SEQUENCE: 34
cgagaagaac ggatagctga a                                              21
```

<210> SEQ ID NO 35
<211> LENGTH: 21
<212> TYPE: DNA
<213> ORGANISM: Artificial Sequence
<220> FEATURE:
<223> OTHER INFORMATION: OTUD6B shRNA clone 2

<400> SEQUENCE: 35
cgatgagact aatgcagtga a                                         21

<210> SEQ ID NO 36
<211> LENGTH: 21
<212> TYPE: DNA
<213> ORGANISM: Artificial Sequence
<220> FEATURE:
<223> OTHER INFORMATION: OTUD6B shRNA clone 3

<400> SEQUENCE: 36
gcaaagctac taacaggtgt t                                         21

<210> SEQ ID NO 37
<211> LENGTH: 21
<212> TYPE: DNA
<213> ORGANISM: Artificial Sequence
<220> FEATURE:
<223> OTHER INFORMATION: OTUD6B shRNA clone 4

<400> SEQUENCE: 37
gctgactact aaggagaata a                                         21

<210> SEQ ID NO 38
<211> LENGTH: 21
<212> TYPE: DNA
<213> ORGANISM: Artificial Sequence
<220> FEATURE:
<223> OTHER INFORMATION: OTUD6B shRNA clone 5

<400> SEQUENCE: 38
cagggcatga agaatgctgt t                                         21

<210> SEQ ID NO 39
<211> LENGTH: 21
<212> TYPE: DNA
<213> ORGANISM: Artificial Sequence
<220> FEATURE:
<223> OTHER INFORMATION: OTUD7B shRNA clone 1

<400> SEQUENCE: 39
cgggacttga tgctgcggaa a                                         21

<210> SEQ ID NO 40
<211> LENGTH: 21
<212> TYPE: DNA
<213> ORGANISM: Artificial Sequence
<220> FEATURE:
<223> OTHER INFORMATION: OTUD7B shRNA clone 2

<400> SEQUENCE: 40
cggtcccatg tctcctccaa t                                         21

<210> SEQ ID NO 41
<211> LENGTH: 21
<212> TYPE: DNA
<213> ORGANISM: Artificial Sequence
<220> FEATURE:
<223> OTHER INFORMATION: OTUD7B shRNA clone 3

```
<400> SEQUENCE: 41
cccaactcag accaaatgca a                                              21

<210> SEQ ID NO 42
<211> LENGTH: 21
<212> TYPE: DNA
<213> ORGANISM: Artificial Sequence
<220> FEATURE:
<223> OTHER INFORMATION: OTUD7B shRNA clone 4

<400> SEQUENCE: 42
gcaaggaggc taaacaaagt t                                              21

<210> SEQ ID NO 43
<211> LENGTH: 21
<212> TYPE: DNA
<213> ORGANISM: Artificial Sequence
<220> FEATURE:
<223> OTHER INFORMATION: OTUD7B shRNA clone 5

<400> SEQUENCE: 43
cctgtatatg agagccttga a                                              21

<210> SEQ ID NO 44
<211> LENGTH: 21
<212> TYPE: DNA
<213> ORGANISM: Artificial Sequence
<220> FEATURE:
<223> OTHER INFORMATION: USP2 shRNA clone 1

<400> SEQUENCE: 44
ccgcgctttg ttggctataa t                                              21

<210> SEQ ID NO 45
<211> LENGTH: 21
<212> TYPE: DNA
<213> ORGANISM: Artificial Sequence
<220> FEATURE:
<223> OTHER INFORMATION: USP2 shRNA clone 2

<400> SEQUENCE: 45
gctcacaaca tttgtgaact t                                              21

<210> SEQ ID NO 46
<211> LENGTH: 21
<212> TYPE: DNA
<213> ORGANISM: Artificial Sequence
<220> FEATURE:
<223> OTHER INFORMATION: USP2 shRNA clone 3

<400> SEQUENCE: 46
cccattgcta agcgaggtta t                                              21

<210> SEQ ID NO 47
<211> LENGTH: 21
<212> TYPE: DNA
<213> ORGANISM: Artificial Sequence
<220> FEATURE:
<223> OTHER INFORMATION: USP2 shRNA clone 4

<400> SEQUENCE: 47
ccatgctgtt tacaacctgt a                                              21

<210> SEQ ID NO 48
```

```
<211> LENGTH: 21
<212> TYPE: DNA
<213> ORGANISM: Artificial Sequence
<220> FEATURE:
<223> OTHER INFORMATION: USP2 shRNA clone 5

<400> SEQUENCE: 48
cctcggcgtt tgcatttgta a                                           21

<210> SEQ ID NO 49
<211> LENGTH: 21
<212> TYPE: DNA
<213> ORGANISM: Artificial Sequence
<220> FEATURE:
<223> OTHER INFORMATION: USP29 shRNA clone 1

<400> SEQUENCE: 49
ctggtgaaga ataacgagca a                                           21

<210> SEQ ID NO 50
<211> LENGTH: 21
<212> TYPE: DNA
<213> ORGANISM: Artificial Sequence
<220> FEATURE:
<223> OTHER INFORMATION: USP29 shRNA clone 2

<400> SEQUENCE: 50
ccctcaatca gtctacagaa t                                           21

<210> SEQ ID NO 51
<211> LENGTH: 21
<212> TYPE: DNA
<213> ORGANISM: Artificial Sequence
<220> FEATURE:
<223> OTHER INFORMATION: USP29 shRNA clone 3

<400> SEQUENCE: 51
tgtgtggagt atcttggtgt a                                           21

<210> SEQ ID NO 52
<211> LENGTH: 21
<212> TYPE: DNA
<213> ORGANISM: Artificial Sequence
<220> FEATURE:
<223> OTHER INFORMATION: USP29 shRNA clone 4

<400> SEQUENCE: 52
gcagtgtatt gaggagagca t                                           21

<210> SEQ ID NO 53
<211> LENGTH: 21
<212> TYPE: DNA
<213> ORGANISM: Artificial Sequence
<220> FEATURE:
<223> OTHER INFORMATION: USP29 shRNA clone 5

<400> SEQUENCE: 53
ccactttaga gatagggcaa t                                           21

<210> SEQ ID NO 54
<211> LENGTH: 21
<212> TYPE: DNA
<213> ORGANISM: Artificial Sequence
<220> FEATURE:
<223> OTHER INFORMATION: USP37 shRNA clone 4

<400> SEQUENCE: 54
```

```
gctaccgagt taagtcttca a                                              21

<210> SEQ ID NO 55
<211> LENGTH: 21
<212> TYPE: DNA
<213> ORGANISM: Artificial Sequence
<220> FEATURE:
<223> OTHER INFORMATION: USP37 shRNA clone 3

<400> SEQUENCE: 55
ccctaacttc tctggcctat t                                              21

<210> SEQ ID NO 56
<211> LENGTH: 21
<212> TYPE: DNA
<213> ORGANISM: Artificial Sequence
<220> FEATURE:
<223> OTHER INFORMATION: USP37 shRNA clone 2

<400> SEQUENCE: 56
gagaataaag tcagcctagt a                                              21

<210> SEQ ID NO 57
<211> LENGTH: 21
<212> TYPE: DNA
<213> ORGANISM: Artificial Sequence
<220> FEATURE:
<223> OTHER INFORMATION: USP37 shRNA clone 1

<400> SEQUENCE: 57
ccggatttgc agaagatgat a                                              21

<210> SEQ ID NO 58
<211> LENGTH: 21
<212> TYPE: DNA
<213> ORGANISM: Artificial Sequence
<220> FEATURE:
<223> OTHER INFORMATION: USP37 shRNA clone 5

<400> SEQUENCE: 58
cggagtggct acatcttctt t                                              21

<210> SEQ ID NO 59
<211> LENGTH: 2577
<212> TYPE: DNA
<213> ORGANISM: Homo sapiens

<400> SEQUENCE: 59
atggatctga caaaaatggg catgatccag ctgcagaacc ctagccaccc cacggggcta     60
ctgtgcaagg ccaaccagat gcggctggcc gggactttgt gcgatgtggt catcatggtg    120
gacagccagg agttccacgc ccaccggacg gtgctggcct gcaccagcaa gatgtttgag    180
atcctcttcc accgcaatag tcaacactat actttggact cctctcgcc aaagaccttc    240 cagcagattc tggagtatgc atatacagcc acgctgcaag ccaaggcgga ggacctggat    300
gacctgctgt atgcggccga gatcctggag atcgagtacc tggaggaaca gtgcctgaag    360
atgctggaga ccatccaggc ctcagacgac aatgacacgg aggccaccat ggccgatggc    420
ggggccgagg aagaagagga ccgcaaggct cggtacctca gaacatctt catctcgaag    480 cattccagcg aggagagtgg gtatgccagt gtggctggac agagcctccc tgggcccatg    540
gtggaccaga gcccttcagt ctccacttca tttggtcttt cagccatgag tcccaccaag    600
```

-continued

```
gctgcagtgg acagtttgat gaccatagga cagtctctcc tgcagggaac tcttcagcca    660
cctgcagggc ccgaggagcc aactctggct gggggtgggc ggcaccctgg ggtggctgag    720
gtgaagacgg agatgatgca ggtggatgag gtgcccagcc aggacagccc tggggcagcc    780
gagtccagca tctcaggagg gatggggggac aaggttgagg aaagaggcaa agaggggcct   840
gggaccccga ctcgaagcag cgtcatcacc agtgctaggg agctacacta tgggcgagag    900
gagagtgccg agcaggtgcc accccagct gaggctggcc aggcccccac tggccgacct     960
gagcacccag caccccgcc tgagaagcat ctgggcatct actccgtgtt gcccaaccac    1020
aaggctgacg ctgtattgag catgccgtct tccgtgacct ctggcctcca cgtgcagcct   1080
gccctggctg tctccatgga cttcagcacc tatgggggc tgctgcccca gggcttcatc    1140
cagagggagc tgttcagcaa gctgggggag ctggctgtgg gcatgaagtc agagagccgg   1200
accatcggag agcagtgcag cgtgtgtggg gtcgagcttc ctgataacga ggctgtggag   1260
cagcacagga agctgcacag tgggatgaag acgtacgggt gcgagctctg cgggaagcgg   1320
ttcctggata gtttgcggct gagaatgcac ttactggctc attcagccat tgagacccag   1380
agcagcagtt ctgaagagat agtgcccagc cctccctcgc caccccctct accccgcatc   1440
tacaagcctt gctttgtctg tcaggacaag tcctcaggct accactatgg ggtcagcgcc   1500
tgtgagggct gcaagggctt cttccgccgc agcatccaga agaacatggt gtacacgtgt   1560
caccgggaca agaactgcat catcaacaag gtgacccgga accgctgcca gtactgccga   1620
ctgcagaagt gctttgaagt gggcatgtcc aaggagtctg tgagaaacga ccgaaacaag   1680
aagaagaagg aggtgcccaa gcccgagtgc tctgagagct acacgctgac gccggaggtg   1740
ggggagctca ttgagaaggt gcgcaaagcg caccaggaaa ccttccctgc cctctgccag   1800
ctgggcaaat acactacgaa caacagctca gaacaacgtg tctctctgga cattgacctc   1860
tgggacaagt tcagtgaact ctccaccaag tgcatcatta agactgtgga gttcgccaag   1920
cagctgcccg gcttcaccac cctcaccatc gccgaccaga tcaccctcct caaggctgcc   1980
tgcctggaca tcctgatcct gcggatctgc acgcggtaca cgcccgagca ggacaccatg   2040
accttctcgg acgggctgac cctgaaccgg acccagatgc acaacgctgg cttcggcccc   2100
ctcaccgacc tggtctttgc cttcgccaac cagctgctgc ccctggagat ggatgatgcg   2160
gagacggggc tgctcagcgc catctgcctc atctgcggag accgccagga cctggagcag   2220
ccggaccggg tggacatgct gcaggagccg ctgctggagg cgctaaaggt ctacgtgcgg   2280
aagcggaggc ccagccgccc ccacatgttc cccaagatgc taatgaagat tactgacctg   2340
cgaagcatca gcgccaaggg ggctgagcgg gtgatcacgc tgaagatgga gatcccgggc   2400
tccatgccgc ctctcatcca ggaaatgttg gagaactcag agggcctgga cactctgagc   2460
ggacagccgg ggggtggggg gcgggacggg ggtggcctgg ccccccgcc aggcagctgt   2520
agccccagcc tcagccccag ctccaacaga agcagcccgg ccacccactc cccgtga     2577
```